(12) United States Patent
Chamdani et al.

(10) Patent No.: US 11,210,834 B1
(45) Date of Patent: *Dec. 28, 2021

(54) ARTICLE OF CLOTHING FACILITATING CAPTURE OF MOTIONS

(71) Applicant: TuringSense Inc., Santa Clara, CA (US)

(72) Inventors: Joseph I. Chamdani, Santa Clara, CA (US); Wade Lagrone, Oakland, CA (US); Pietro Garofalo, Forli (IT); Gabriele Ligorio, Pisa (IT); Michele Raggi, Forli (IT); Josh Sole, Santa Clara, CA (US)

(73) Assignee: Turingsense Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/687,647

(22) Filed: Nov. 18, 2019

Related U.S. Application Data

(63) Continuation-in-part of application No. 16/423,130, filed on May 27, 2019, now Pat. No. 10,672,173, which is a continuation of application No. 16/219,727, filed on Dec. 13, 2018, now Pat. No. 10,304,230, which is a continuation of application No. 15/271,205, filed on Sep. 20, 2016, now Pat. No. 10,157,488.

(60) Provisional application No. 62/768,967, filed on Nov. 18, 2018, provisional application No. 62/221,502, filed on Sep. 21, 2015.

(51) Int. Cl.
 *G06F 3/045* (2006.01)
 *G06T 13/40* (2011.01)
 *G06F 3/01* (2006.01)

(52) U.S. Cl.
 CPC .............. *G06T 13/40* (2013.01); *G06F 3/011* (2013.01); *G06F 3/014* (2013.01); *G06F 3/017* (2013.01)

(58) Field of Classification Search
 CPC .......... G06T 13/40; G06F 3/011; G06F 3/014; G06F 3/017; G06F 1/163
 See application file for complete search history.

(56) References Cited

U.S. PATENT DOCUMENTS

| | | | |
|---|---|---|---|
| 9,043,004 B2* | 5/2015 | Casillas | A61B 5/6804 700/91 |
| 10,250,597 B2* | 4/2019 | Hoyos | G06F 16/955 |
| 10,561,881 B2* | 2/2020 | Matsuura | A41D 1/002 |
| 2014/0172134 A1* | 6/2014 | Meschter | A63B 24/00 700/91 |
| 2015/0366504 A1* | 12/2015 | Connor | A61B 5/6804 600/301 |
| 2015/0370320 A1* | 12/2015 | Connor | A61B 5/1126 345/173 |
| 2016/0072802 A1* | 3/2016 | Hoyos | H04L 63/0861 726/5 |

(Continued)

*Primary Examiner* — Vijay Shankar
(74) *Attorney, Agent, or Firm* — Joe Zheng

(57) ABSTRACT

An article of clothing facilitating capture of motions is described. The clothing has an inner side. A plurality of sensor modules are respectively attached to designated locations on the inner side, where the sensor modules and batteries if not enclosed in the sensor modules are coupled by a plurality of conductive threads embedded in materials of the clothing. These sensor modules are responsible for capturing respective motions corresponding designated body parts when the clothing is worn by a wearer.

13 Claims, 36 Drawing Sheets

(56) References Cited

U.S. PATENT DOCUMENTS

2018/0010902 A1\* 1/2018 Gong ................... A61B 5/1072
2018/0184735 A1\* 7/2018 Longinotti-Buitoni ......................
 A61B 5/6843

\* cited by examiner

LEFT (a) Grid search algorithm working principle for one body segment (right upper arm): angular grid (in blue), anatomical longitudinal axis (green), mediolateral direction initial guess (red) and refined mediolateral direction (black); RIGHT (b) Cost function over the grid for four body segments left and right upper arm and left and right upper leg

ARTICLE OF CLOTHING FACILITATING CAPTURE OF MOTIONS

CROSS REFERENCE TO RELATED APPLICATIONS

This application is a continuation-in-part of co-pending U.S. application Ser. No. 16/423,130, entitled "System and method for capturing and analyzing motions to be shared", filed on May 27, 2019, which is a continuation of U.S. application Ser. No. 16/219,727, entitled "System and method for capturing and analyzing motions to render a human avatar animation", filed on Dec. 13, 2018, now U.S. Pat. No. 10,304,230, which is a continuation of U.S. application Ser. No. 15/271,205, entitled "System and method for capturing and analyzing motions", filed on Sep. 20, 2016, now U.S. Pat. No. 10,157,488, which claims the priority of U.S. Prov. App. Ser. No. 62/221,502, entitled "System and method for capturing and analyzing complex motions", filed on Sep. 21, 2015. This application also claims the benefits of U.S. provisional application No. 62/768,967, entitled "Motion control based on artificial intelligence", filed on Nov. 18, 2018, which is hereby incorporated by reference for all purposes.

BACKGROUND OF THE INVENTION

Field of the Invention

The present invention is generally related to motion controls and more particularly related to methods and systems for motion controls based on artificial intelligence and providing instructions to a user to mimic motions performed by an instructor. The present invention is also particularly related to sensorized electronic garments (eGarments) to facilitate the capture of motions performed by a wearer and various techniques to derive motions of the wearer based on data from sensors embedded in eGarments.

Description of the Related Art

Current wearable devices in the market are limited to tracking simple repetitive activities like walking, running, and swimming. They count simple statistics like how many/much steps/strokes, calories, and heart rates per period. They are prone to inaccuracies and less beneficial if used for complex sports like yoga, fitness, golf, and tennis. Some efforts are attempting to address the problem by adding a 9-axis inertial sensor (e.g., 3-axis gyroscope+3-axis accelerometer+3-axis magnetometer) in the equipment (e.g., racquet, club, bat), or providing 1 or 2 sensors in a user (e.g., placed near a wrist, ankle, or ear). What users get however are still limited to "after-the-fact" statistics (e.g., repetition count, speed, or cadence), some numbers that are less useful to tell what the user did or did not do correctly, how to improve the technique or reduce injury risk.

Thus there is a great need for methodologies or systems that are capable of motion management without confining the motions performed by a user, providing real-time feedback and authoritative coaching and/or instruction.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In general, the present invention is related to techniques for motion controls based on artificial intelligence. According to one aspect of the present invention, instructions are provided based on motions performed by a user in reference to motions performed by an instructor. Various parameters or attributes about the motions by the user are analyzed, derived and compared with stored parameters pertaining to motions performed by an authoritative person (i.e., instructor). An animation based on the user or an avatar representing the user is rendered per the motion parameters. Various techniques or algorithms are designed to provide different perspective views of the motions by the user and the instructor and compare the motions or poses by the user and the instructor.

According to another aspect of the present invention, an article of clothing is uniquely designed to capture motions by a wearer (user), where a plurality of sensors or sensor modules are respectively attached to or embedded in different parts of the clothing. Depending on how the sensors or sensor modules operate, specially designed conductive wires are provided within the clothing to provide a communication medium between and/or among the sensors or sensor modules. Depending on implementation, the sensors may communicate with a designated sensor wirelessly or via the medium while the designated sensor communicates wirelessly with an external device. When the clothing is worn by a wearer or user, these embedded sensors facilitate the capture of motions performed by the wearer without confining the wearer to a limited number of motions or poses.

According to another aspect of the present invention, some or all of the sensors are designated to react to certain actions from a user to generate a command signal when the user taps on a specific part of his/her body, where the command signal causes a system (e.g., an external device) to respond to the command signal by, for example, changing or repeating a perspective view of motion or pose being performed by an instructor.

According to still another aspect of the present invention, a library of activities (e.g., tennis or Yoga) is provided in a computing device that allows the user to choose one therefrom to exercise. The library also provides a group of instructors for the chosen activity. A video of a chosen instructor performing the activity is displayed after one of the instructors is chosen so that the user may follow the instructor to perform the activity. The video is modified or enhanced to include an avatar representing the user next to the representation of the instructor so that a comparison of two performing the same activity can be provided.

According to still another aspect of the present invention, a display is provided based on the motions by a user. The display includes at least two avatars representing the user and an instructor, where various perspective views of the two avatars can be provided, errors in motion or pose differences can be highlighted, corrected when the user changes his/her motions, and progressive scores of the comparisons can also be provided.

According to still another aspect of the present invention, a perspective view of comparisons between the user and the instructor performing the same activity is automatically determined to allow the user to correct his/her move so as to reduce or minimize the differences in their moves. The angle of the perspective video may be determined based on a set of procedure specified by the instructor, a possible cause of error by the user in his/her move and a move needed by a body part and etc.

According to yet another aspect of the present invention, a perspective view is automatically provided when the errors are beyond a threshold, where the perspective view is determined based on a largest difference between two corresponding parts in the two avatars and shows the difference between the two corresponding parts.

The present invention may be implemented as a method, a system, an apparatus, a part of a system, and an article of clothing. Different implementations yield different benefits, advantages and objectives. According to one embodiment, the present invention is a motion management system comprising an article of clothing having a layer of material, and a plurality of sensor modules respectively attached to designated locations on the inner side of the clothing. Each of the sensor modules corresponds to a designated body part of a wearer of the clothing. At least one of the sensor modules is designated as a hub module and the rest of the sensor modules are designated as satellite modules. Each of the satellite modules includes a microcontroller, at least an inertial sensor and a transceiver for intercommunication with the hub module. The hub module includes a microcontroller, at least an inertial sensor and a transceiver for intercommunication with the satellite modules and another transceiver for communicating with an external computing device.

According to another embodiment, the present invention is a motion management system comprising an article of clothing having a layer of material, and a plurality of sensor modules respectively attached to designated locations on the layer of material, each of the sensor modules corresponding to a designated body part of a wearer of the clothing, wherein one of the sensor modules is designated as a hub module and the rest of the sensor modules are designated as satellite modules, each of the satellite modules includes an inertial sensor, the hub module includes a microcontroller, at least an inertial sensor and an interface to receive sensing signals from inertial sensors in the satellite modules via respective conductive threads embedded in the layer of material and a transceiver for communicating with an external computing device.

According to still another embodiment, the present invention is a method for motion management. The method comprising receiving in an external device sensing data from a plurality of sensor modules, derive from the sensing data a set of attributes pertaining to motions performed by a user, a player or a wearer of an article of specially designed clothing, and rendering a display showing an avatar representing the wearer, wherein the avatar is animated as the wearer moves. The display may also be rendered to show a representation of another person selected from a list of instructors. The representation is animated based on stored data.

According to still another embodiment, the present invention is a method for comparing motions, the method comprises: rendering in a computing device a first avatar from attributes derived from first motion performed by a user, retrieving from a database a representation of second motion performed by an instructor selected by the user from a list of authoritative instructors, showing on a display screen a display of the first avatar next to the representation; and adjusting the display in a perspective view determined by the user in responding to a request from the user. Depending on implementation, the representation of the instructor may be an animated object or a second avatar rendered from the representation or the attributed from the second motion in data store.

According to still another embodiment, the present invention is a computing device for comparing motions, the computing device comprises: a processor, a transceiver coupled to the processor and receiving sensing data wirelessly from at least one sensor module in a plurality of sensor modules disposed respectively and closely to designated body parts of a user, and a memory space coupled to the processor for storing code. The code executed by the processor causes the computing device to perform operations of: rendering a first avatar from attributes derived from first motion performed by the user, retrieving from a database a representation of second motion performed by an instructor selected by the user from a list of authoritative instructors, showing on a display screen a display of the first avatar next to the representation, and adjusting the display in a perspective view determined by the user in responding to a request from the user.

According to yet another embodiment, the present invention is an article of clothing comprising: a layer of material, a plurality of sensor modules respectively attached to designated locations on the layer of material; and a plurality of conductive threads embedded in materials of the clothing, wherein one or more of the threads provide a communication medium between or among the sensor modules. In a preferable embodiment, the layer of material has an inner side, the sensor modules are respectively attached to designated locations on the inner side of the layer of material.

Other objects, features, benefits and advantages, together with the foregoing, are attained in the exercise of the invention in the following description and resulting in the embodiment illustrated in the accompanying drawings.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE PREFERRED EMBODIMENTS

Figure 1A:
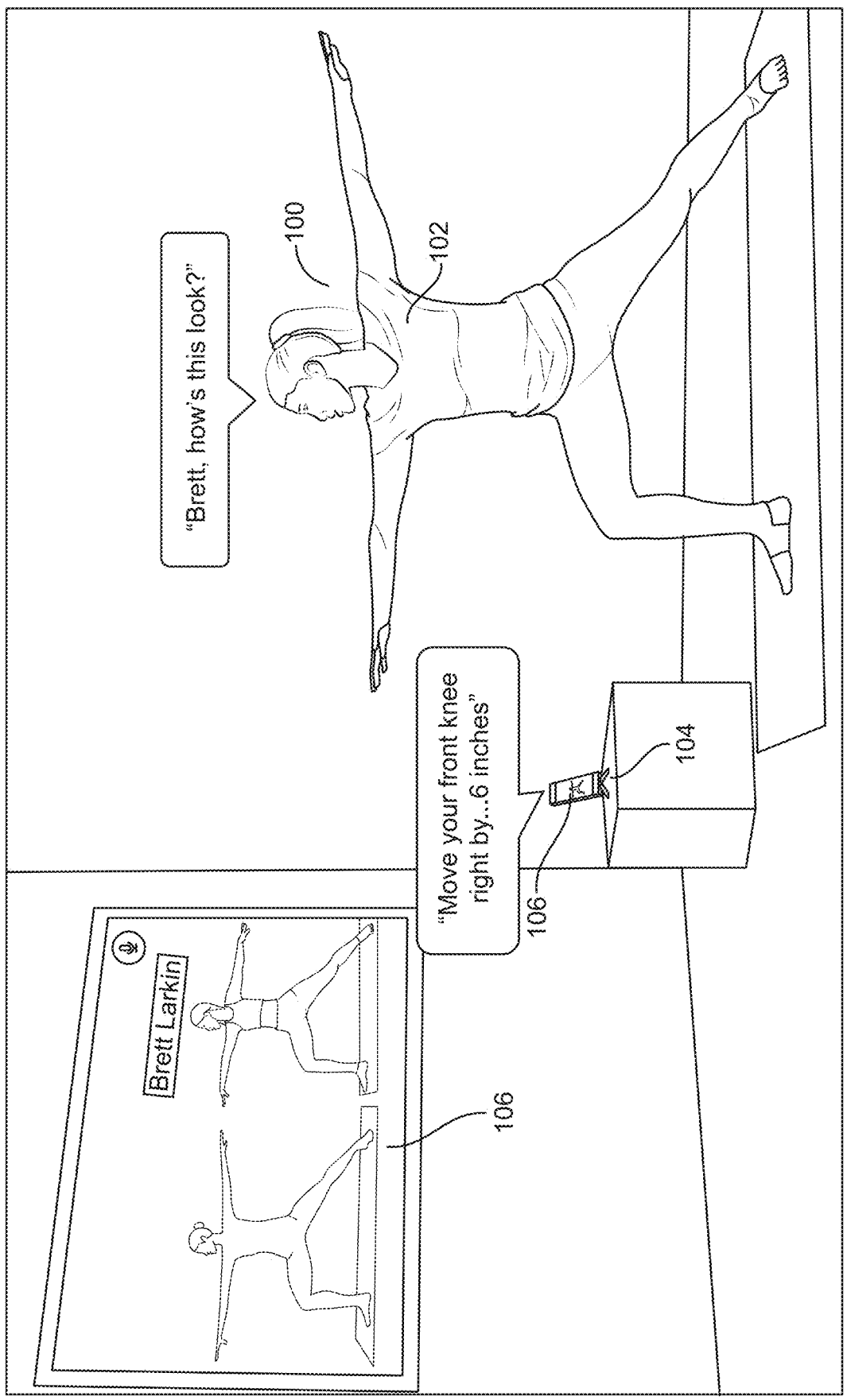
FIG. 1A shows an exemplary configuration in which a user 100 in specially-designed shirt and pants performs a pose or certain motions according to one embodiment of the present invention.

In the following detailed description of the present invention, numerous specific details are set forth in order to provide a thorough understanding of the present invention. However, it will become obvious to those skilled in the art that the present invention may be practiced without these specific details. In other instances, well known methods, procedures, components, and circuitry have not been described in detail to avoid unnecessarily obscuring aspects of the present invention.

The detailed descriptions of the present invention in the following are presented largely in terms of procedures, steps, logic blocks, processing, and other symbolic representations that resemble data processing devices capable of communicating with other devices. These descriptions and representations are the means commonly used by those experienced or skilled in the art to most effectively convey the substance of their work to others skilled in the art. The present invention includes one or more methods and systems for facilitating the management of motions. The methods along with systems including circuits or architecture of computing devices to be described in detail below are a self-consistent sequence of processes or steps leading to one or more desired results. These steps or processes are those requiring physical manipulations of physical quantities. Usually, though not necessarily, these quantities may take the form of electrical signals capable of being stored, transferred, combined, compared, displayed and otherwise manipulated in a computer system or electronic computing devices. It proves convenient at times, principally for reasons of common usage, to refer to these signals as bits, values, elements, symbols, operations, messages, terms, numbers, or the like. It should be borne in mind that all of these similar terms are to be associated with the appropriate physical quantities and are merely convenient labels applied to these quantities. Unless specifically stated otherwise as apparent from the following description, it is appreciated that throughout the present invention, discussions utilizing terms such as "processing" or "sending" or "verifying" or "displaying" or the like, refer to the actions and processes of a computing device that manipulates and transforms data represented as physical quantities within the computing device's registers and memories into other data similarly represented as physical quantities within the computing device or other electronic devices.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

One of embodiments in the present invention is to build a scalable cloud-based motion artificial intelligence (AI) platform (technology or system) with sensorized electronic garments to capture full-body motions performed by a wearer (user) in a 3-dimension space (3D) to give real-time coaching feedback to learn proper motions or poses from an instructor or teacher remotely located or in an application library (or database). With the technology, human motions can be readily digitized into 3D data without using cameras, deployed to mass users for all kinds of creative 3D motion applications in sports, healthcare, AR/VR/gaming, and etc. For example, Yoga is an exemplary sport/exercise application that may practice one embodiment of the present invention. One of the advantages, benefits and objectives in the present invention is to help people to learn quickly how to move or pose properly in fitness, golf, tennis, soccer, dance, physical therapy rehabilitation, and etc.

Yoga will be used as an example or exemplary sport to facilitate the description of the present invention. A system providing Yoga employing one embodiment of the present invention is herein referred to as PIVOT Yoga herein. According to one embodiment, PIVOT Yoga is a system, a method, an apparatus or a part of system, wherein PIVOT Yoga includes at least three elements. 1. An article of clothing or garment (a.k.a., eGarment), worn by a yoga practitioner, is embedded with a plurality of (digital) sensors that observe and transmit the angles and relative positions of body parts of the user in real time and 3D space to an external device (e.g., a smartphone). 2. A mobile application or App, executed in the external device, is designed to receive, process, and interpret sensor data from the sensors, and displays a representation of motions by one of yoga teachers. 3. Within the App, embedded intelligence is specific to each teacher, where the intelligence, also referred to as Motion AI, is what tells a user to which adjustments to his/her yoga pose are needed.

As used herein, any pronoun references to gender (e.g., he, him, she, her, etc.) are meant to be gender-neutral. Unless otherwise explicitly stated, the use of the pronoun "he", "his" or "him" hereinafter is only for administrative clarity and convenience. Additionally, any use of the singular or the plural shall also be construed to refer to the plural or to the singular, respectively, as warranted by the context.

FIG. 1A shows an exemplary configuration in which a user 100 in specially-designed shirt and pants 102 performs a pose or certain motions according to one embodiment of the present invention. As further described below, the shirt and pants 102 include a plurality of sensor modules (preferably not visible), each being affixed to a designated location, preferably inside, of the clothing 102. With a designated App executing in a portable device 104 (iPhone or wearable device), the user 100 (i.e., a wearer of the clothing 102) can view on a display 106 how well she is performing a pose (motion).

Subject to a preference, the user 100 may place such an exemplary device 104 anywhere as long as it can maintain communication with the sensors in the clothing 102. A display 106 may be shown from the device 104 or on a larger screen (e.g., via Chromcast). The user 100 may choose a yoga routine from a list of activities in the App executed in the portable device 104, and then proceed with the routine. As will be further detailed below, the user 100 may further choose an instructor or teacher from a list of available instructors to guide her exercise, where the chosen instructor may be asked for feedback for each pose or motion the user 100 has just performed. The instructor, in her own voice, will then verbally tell or show the user, for example, which body part to move, in which direction, and how far. In one embodiment, the portable device 104 may provide verbal instructions from the chosen instructor or show a video, where the user may control the video in various ways, e.g., voice command or taping on some body parts, and at any point during a pose, ask for comparison between the motions of herself and the chosen instructor.

Figure 1B:
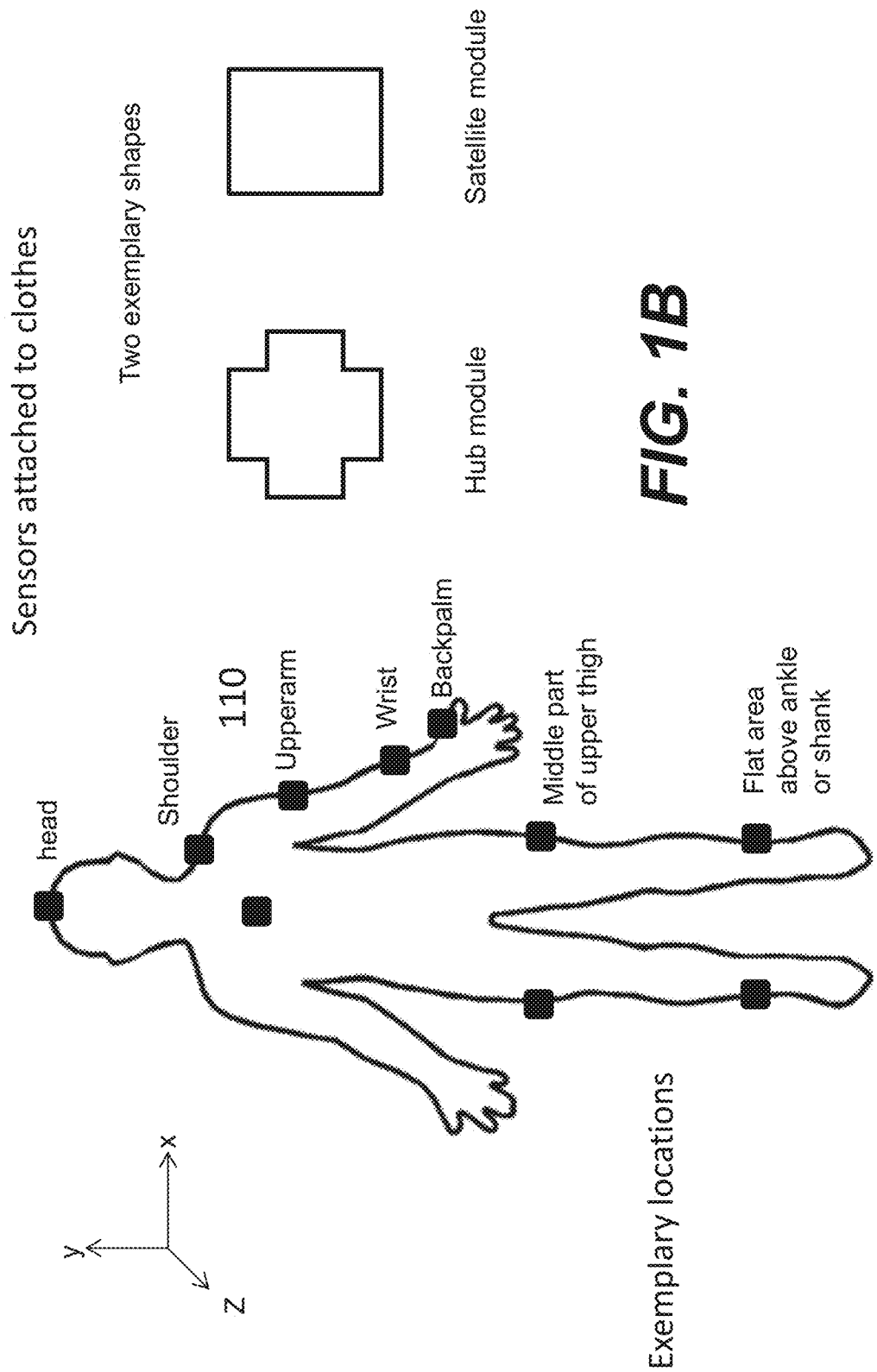
FIG. 1B shows there are a number of sensor devices, sensor modules or simply sensors placed respectively near certain human body parts.

FIG. 1B shows there are a number of sensor devices, sensor modules or simply sensors 100 to be placed respectively near certain human body parts. According to one embodiment, these sensors are affixed to respective designated locations within the clothes 102 corresponding to designated human body parts, for example, one sensor is responsible for monitoring a chest, another sensor is responsible for monitoring an upper arm, still another sensor is responsible for monitoring a flat area just above an ankle. Depending on implementation, each of the sensors includes one or more inertial sensors that produce sensing signals when the sensors are caused to move around with the wearer. The sensing signals are sampled periodically (e.g., every 10 millisecond) to produce sensing samples or data.

In one embodiment, the portable device 104 executing an App is caused to receive or collect some or all the sensor samples from the sensors and track at every sample point if needed. A system is remotely located with respect to but communicates with the portable device, wherein the system is referred to as a server, a cloud computer or simply cloud, and configured or designed to perform motion analysis by processing a set of raw sensor samples received remotely from one, more or all of the sensors (via the portable device), and derive joint angle outputs to detect start/end of motion, classify a motion type (e.g., forehand topspin, backhand slice, flat serve, etc.) and compute important attributes of the motion (e.g., speed, mass, distance, volume, velocity, acceleration, force, and displacement in scalar or vector). The body segment frames and motion analysis attributes are then sent to a designated App (e.g., Yoga App) running in a mobile device, for 3D graphics rendering into a human avatar, animation and motion chart analysis. Depending on implementation, some or all of the functions in the system may be performed within the portable device 104.

FIG. 1B also shows two exemplary types of the sensor modules, a satellite module and a hub module. For ease of identification in one embodiment, the hub module or hub is designed to have a unique shape, different from the rest of the satellite modules. The hub module is made in a distinct "+" medic shape in one embodiment. In some embodiments, the satellite modules connect wirelessly to a single Hub module, for example, via Wi-Fi, Bluetooth, and etc. In one embodiment, the modules may communicate via a proprietary high-speed 2.4 GHz protocol. For some sport (e.g., tennis), the hub module may be typically disposed near the chest location and is configured to combine the sensor data with the same timestamp and streams, for example, via Wi-Fi or Wi-Fi-Direct to a cloud datacenter or a mobile device (phone, tablet, or laptop). In another embodiment, as will be further described below, the modules may communicate via a communication medium (e.g. conductive threads embedded in an article of clothing).

In one embodiment, each of the satellite modules includes a microcontroller, at least an inertial sensor and a transceiver for intercommunication with the hub module that includes a microcontroller, at least an inertial sensor and a transceiver for intercommunication with the satellite modules and another transceiver for communicating with an external computing device (e.g., the portable device). Each of the sensor modules produces sensing data at a predefined frequency when a user makes moves, the sensing data from the satellite modules are received in the hub module and combined with the sensing data generated within the hub module and transported wirelessly to the external device designed to derive the motion of the user performing activities and facilitate a comparison between the derived motion with stored motion to illustrate a difference between the motion made by the user and motion made by another person.

In another embodiment, each of the satellite modules includes an inertial sensor while the hub module includes a microcontroller, an inertial sensor and an interface for intercommunication with the inertial sensors in the satellite modules and a transceiver for communicating with an external computing device (e.g., the portable device). Each of the inertial sensors produces sensing signals when a user makes moves, the sensing signals from the inertial sensors are received in the hub module via a communication medium (e.g., the conductive threads) and combined with the sensing signal generated within the hub module. The sensing signals are sampled at a predefined frequency and transported wirelessly to the external device designed to derive the motion of the user performing activities and facilitate a comparison between the derived motion with stored motion to illustrate a difference between the motion made by the user and motion made by another person.

Figure 1C:
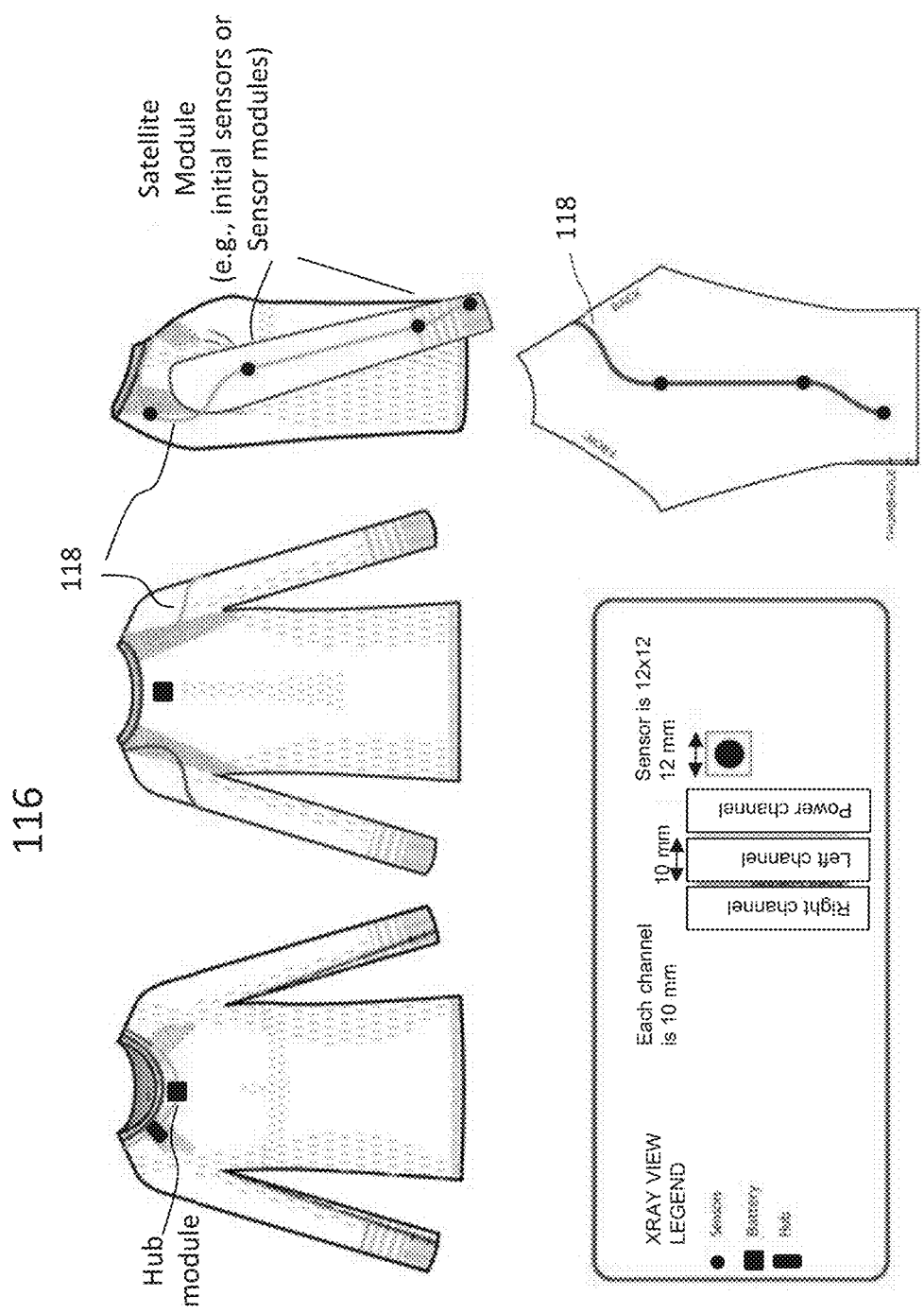
FIG. 1C shows an exemplary layout of locations of the sensors on a long-sleeve shirt.
Figure 1D:
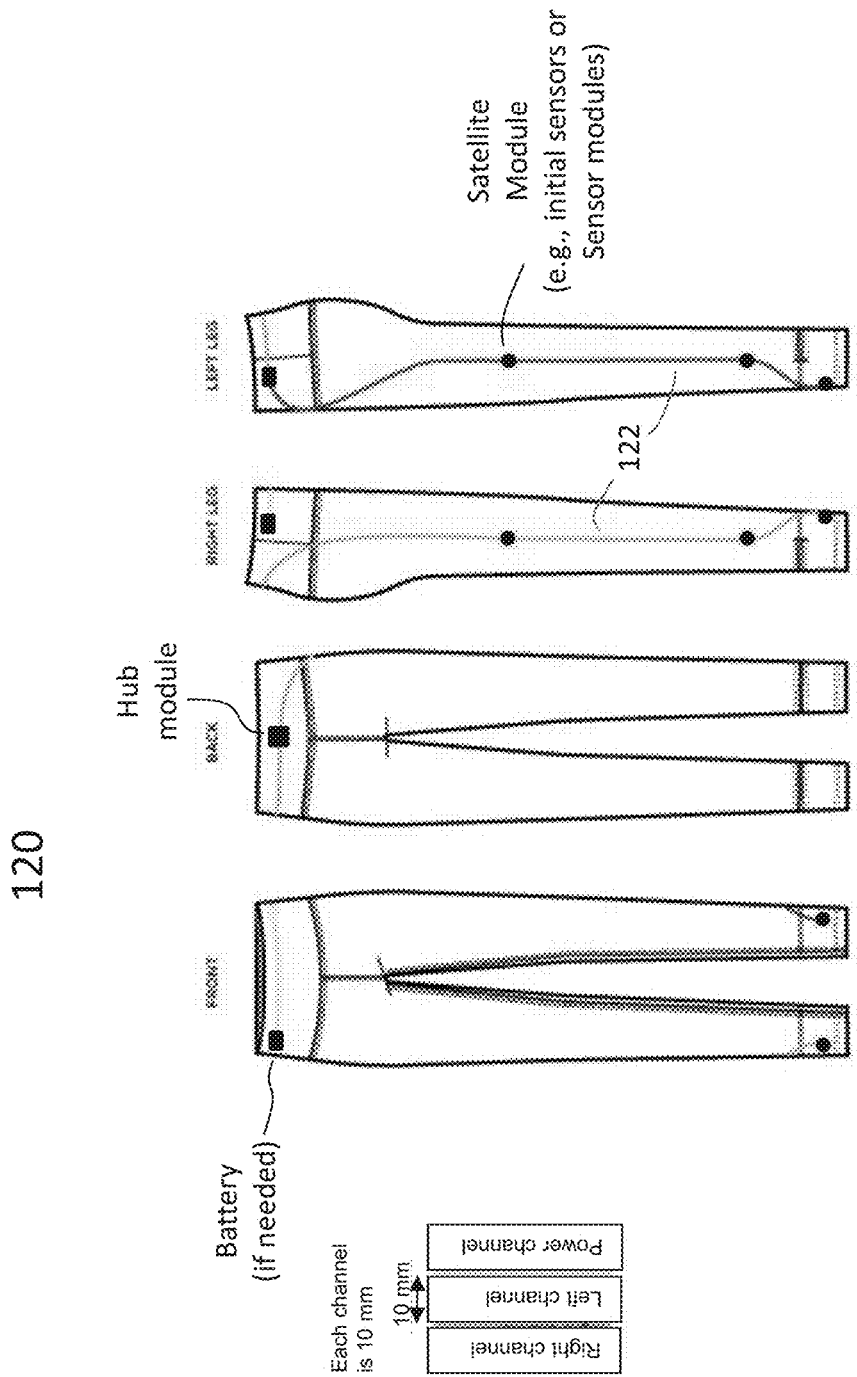
FIG. 1D shows an exemplary layout of locations of the sensors on a pair of pants.

According to one embodiment, an article of clothing, also referred to herein as sensorized eGarments (washable), body motions can be captured and transmitted to an external device so that an authoritative teacher may be engaged to dynamically, in real-time, instruct a user how to improve his motions, for nearly anything from sports to physical therapy. An exemplary sensor module may be, but not limited to, an inertial sensor, such an inertial sensor may be a 9-axis inertial sensor having accelerometer, gyroscope, and magnetometer, or a 6-axis inertial sensor having only accelerometer and gyroscope. Each sensor is placed in a specific location on the inner side of the garment to track the motion of every major limb (bone, body part or body segment). FIG. 1C shows an exemplary layout 116 of locations of the sensors on a long-sleeve shirt, these sensors are located specifically to capture the motion of a particular body part (e.g., a finger or a forearm), where a hub sensor is to be disposed near the chest area of a human body when the shirt is worn. FIG. 1D shows an exemplary layout 120 of locations of the sensors on a pair of pants, these sensors are located specifically to capture the motion of a particular body part (e.g., a knee or an ankle), where a hub sensor is to be disposed near the waist area of a human body. Depending on implementation, one or more batteries (e.g., button batteries) are also embedded in the clothes.

According to one embodiment, a specially designed conductive thread 118 or 122 is used in the clothing to provide connections between batteries and the sensor modules if the batteries are not within each of the sensor modules, and between the hub module and satellite modules. The conductive thread 118 or 122 has textile properties like a regular yarn, composed of low-resistivity (less than 1.5 Ohms per meter) copper core with nano fiber insulation and capable of transmitting high speed electrical signal (up to 10 Mbits per second). In one embodiment, the diameter of the conductive thread 118 or 122 is only 0.32 millimeters. In another embodiment, the conductive thread 118 or 122 goes a zigzag pattern to allow more stretches when needed. When worn, the eGarments look and feel like regular athletic-leisure clothes (athleisure) with the electronics hidden and unfelt.

With the voice capabilities on the portable device, a user is able to pause, resume, skip forward, freeze a video provided by the app. For example, a video or an avatar showing a perfect pose can be paused or repeated, or viewed from different perspectives. The user may ask for feedback while the video of an authoritative teacher is running. Depending on implementation, there are two ways to do this with voice and/or gestures. Without using a wake word, a user, after a one-time setup routine, can simply issue a command within earshot of his phone. The user can issue commands that the system pays attention to as the system is trained to recognize only his voice in one embodiment. As far as the gestures are concerned, since the clothes worn by the user are sensorized, the user may double-tap on various places on his body as a way of controlling the app. In one embodiment, double-tapping on the left hand pauses or resumes the video, double-tapping on the right hand skips to the next chapter in the video, and double-tapping on the chest sensor asks the system for feedback. In another embodiment, a gesture is designed to freeze an avatar in a video. In still another embodiment, one of the sensors (e.g., the one on the waist) is designed to signal a pause of the avatar or feedback of a chosen instructor.

Figure 2:
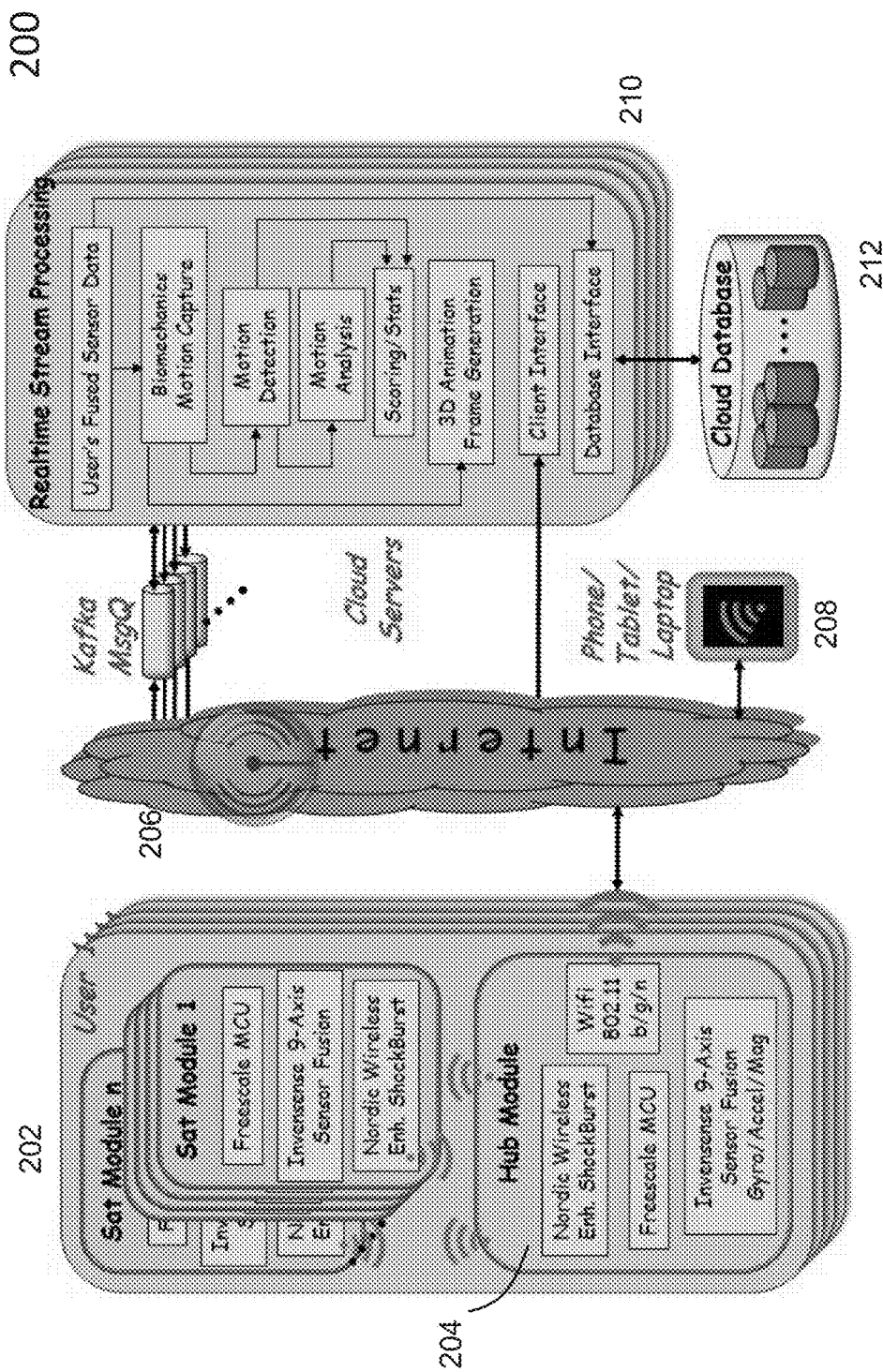
FIG. 2 shows a systemic functional block diagram according to one embodiment of the present invention.

FIG. 2 shows a systemic functional block diagram 200 according to one embodiment of the present invention. A user wears a set of garments embedded with sensor modules 202. The number of sensor modules 202 and placement can be determined depending on a target application and types of motion to be captured and analyzed. According to one embodiment, each sensor module comprises:

- a 9-axis sensor chip having integrated 3-axis gyroscope, 3-axis accelerometer, 3-axis magnetometer, such as those manufactured by Invensense;
- a 32-bit ARM Cortex M4F microcontroller (MCU) with floating point arithmetic unit (FPU) to perform floating-point math-intensive sensor fusion processing at every sensor module, such as those manufactured by Freescale; and
- a wireless chip with embedded 32-bit ARM Cortex M0 MCU to support 2 Mbps wireless communication, such as a Nordic 2.4 GHz wireless chip.

In one embodiment, the wireless chip is based on a proprietary and enhanced Shockburst protocol, which has been deployed for medical/industrial devices. Other standard wireless protocols like Bluetooth/BLE, Ant+ and ZigBee may also be employed. One of the sensor modules 202 is designed to function as a hub 204 of all the satellite sensor modules, controlling and collecting sensor data from the satellite sensor modules. The sensor data from the satellite sensor modules are received and combined with the sensor data generated in the hub 204 into one record having the same timestamp and streamed out to the cloud or the portable device. Typically, the sensor data sampling rate is at 100 Hz, producing gyro x/y/z, accel x/y/z, mag x/y/z, and quaternion w/x/y/z values for each satellite every 10 milliseconds. To get robust data bandwidth and wireless distance to a Wi-Fi router/hotspot, the system may include a Wi-Fi module supporting 802.11b/g/n. In the absence of Wi-Fi router/hotspot, the hub module can stream the sensor data directly to a mobile device 208 (e.g., smartphone/tablet/laptop), for example, via Wi-Fi-Direct protocol. If the mobile device 208 has limited computing resources compared to one or more cloud servers 210, motion capture/analysis may be performed based on reduced information from the sensor modules, but overall still delivering the benefits in the present invention.

In the presence of an Internet connection 206 to a cloud datacenter (e.g., the servers 210), the captured and combined sensor data records are streamed continuously to the cloud datacenter. The data stream queuing and processing may use a framework suitable for real-time stream analytics and having sub-second response time. In one embodiment, the system uses open-source software components, such as Kafka (for message queuing), Jetty (for application session management), and Rserve (for executing R math programs).

With a Kafka framework, the system can queue sensor data streaming from thousands to millions of users, while maintaining low latency requirement for real-time processing. Multiple sensor records may be batched to be processed by the known R math program. One or more R processes may be dedicated for each user to compute the following: Joint angle estimate of each joint based on multi-sensor data and human biomechanics model, rotational direction values of corresponding body segments, detection of the start, middle, end, and type of a motion that is unique to a target application, all based on a sequence of multi-sensor samples (called frames).

For example in tennis, a motion could be a forehand topspin with start frame at ready position, middle frame at ball contact, and end frame at completion of swing follow through. The motion is analyzed for different attributes or statistics, such as (for tennis) number of repetitions, footwork quality metrics (number of steps before ball contact, knee bend angle, balance), power metrics (swing speed, hand acceleration, ball strike zone), injury risk analysis (elbow, shoulder, wrist, back, knee), and etc., all based on the available joint angles, approximate rotation values of all 21 segments of human skeleton (wire body) that is ready to be rendered and animated by a 3D graphics software like Unity (commercially available 3D game engine software).

To complete the streaming, the output of various (joint angle) processing and motion attributes/stats can be streamed out to a user associated portable device to be further processed for live avatar animation and chart views. For playback and data analytics, every user's recording session may be stored in a cloud database or in the portable device. Both the raw sensor data input and output results (e.g., joint angle frames, motion attributes/stats) can be part of the session record. For animation playback and chart views, the output data may be retrieved and sent to a mobile device. When there is enhancement or addition to the motion capture and motion analysis algorithms, the system can re-generate the output results from the original input data.

The overall system stack comprises layers of hardware, firmware, wireless network, cloud infrastructure, real-time streaming software, biomechanics motion algorithms, database, big data analytics, 3D graphics, and a user interface. The following table summarizes the various aspects of the system.

| Requirement | System Feature |
|---|---|
| 1. Capture and analyze human motions with or without camera | Employ inertial sensor chips in smartphones and wearables to track movements. Multiple inertial sensors may track movement of body segments. To get better sensor fusion and positioning accuracy, a processor is employed to integrate all 3 micro-electro-mechanical (MEM) accelerometer, gyroscope, and magnetometer. To further improve human motion capture and analysis, biomechanics modeling and knowledge of the target application's activities are combined. |
| 2. Instant bio-mechanics feedback | System performs high-speed algorithms to analyze motions based on human biomechanics model, joint angles, raw sensor data, and sensor fusion. System incorporates proper biomechanics knowledgebase and patterns into the motion library to compare with, based on the specifics of target application. These algorithms require substantial mathematical computations. To give instant feedback in sub-second, the system provides a real-time stream processing in the cloud for scalable computing. |
| 3. Injury prevention analysis | The system may incorporate injury analysis and motion library patterns/signatures based on studies in biomechanics, physical therapy/rehabilitation, sports medicine, and experiments in the target application area. The system may continuously add more injury patterns into the motion library and algorithms and allow users to add their own injury patterns to recognize possible injury. |
| 4. Live remote motion monitoring or coaching | In one embodiment, the system leverages the cloud capabilities to enable real-time motion monitoring of a user by other authorized users (coach, doctor, supervisor) from any distant places. Unlike video monitoring, the sensor stream bandwidth requirement may be several orders of magnitude less. |

-continued

| Requirement | System Feature |
|---|---|
| 5. Share motion recordings with authorized users | In one embodiment, the system leverages the cloud infrastructure to share motion recordings with other authorized users. The system may record both the raw sensor data input and output results (animation frames, motion attributes). When there is enhancement or addition to the motion capture and motion analysis algorithms, the system can re-generate the output results from the original input data. |
| 6. Data analytics insight | The system may store all user profiles and recordings in the cloud's scalable database/storage. The system may deploy big data analytics tools and search queries to gain insight information upon request on user's own data, or anonymous business intelligence. |
| 7. Scalable and adaptable to many target applications | The system platform is based on an architecture with common building blocks that can scale and adapt to customization and many target applications. In one embodiment, the system leverages cloud's "infinite" computing resources to scale increased application complexity, the number of active users, concurrent sessions at peak usage, and newly developed applications. The system may implement on-demand cloud resource management with load balancing to handle changing requirements and demands. |
| 8. Affordable | The system may optimize COGS (cost of goods sold) by choosing commodity/volume hardware components, cost-efficient contract manufacturers, and license-free open source software packages. The system may optimize operational costs through on-demand cloud resources. |
| 9. Easy to use | The system may use an intuitive UI (user interface) with game technology where users of all ages can operate easily without a manual or complex instructions. The system may select features that give most benefits to users and present the feature capabilities in multi-level UI, starting from simple to deep analysis. The system may use sensor packaging and harness designed for simplicity and ease of use. |

Figure 3A:
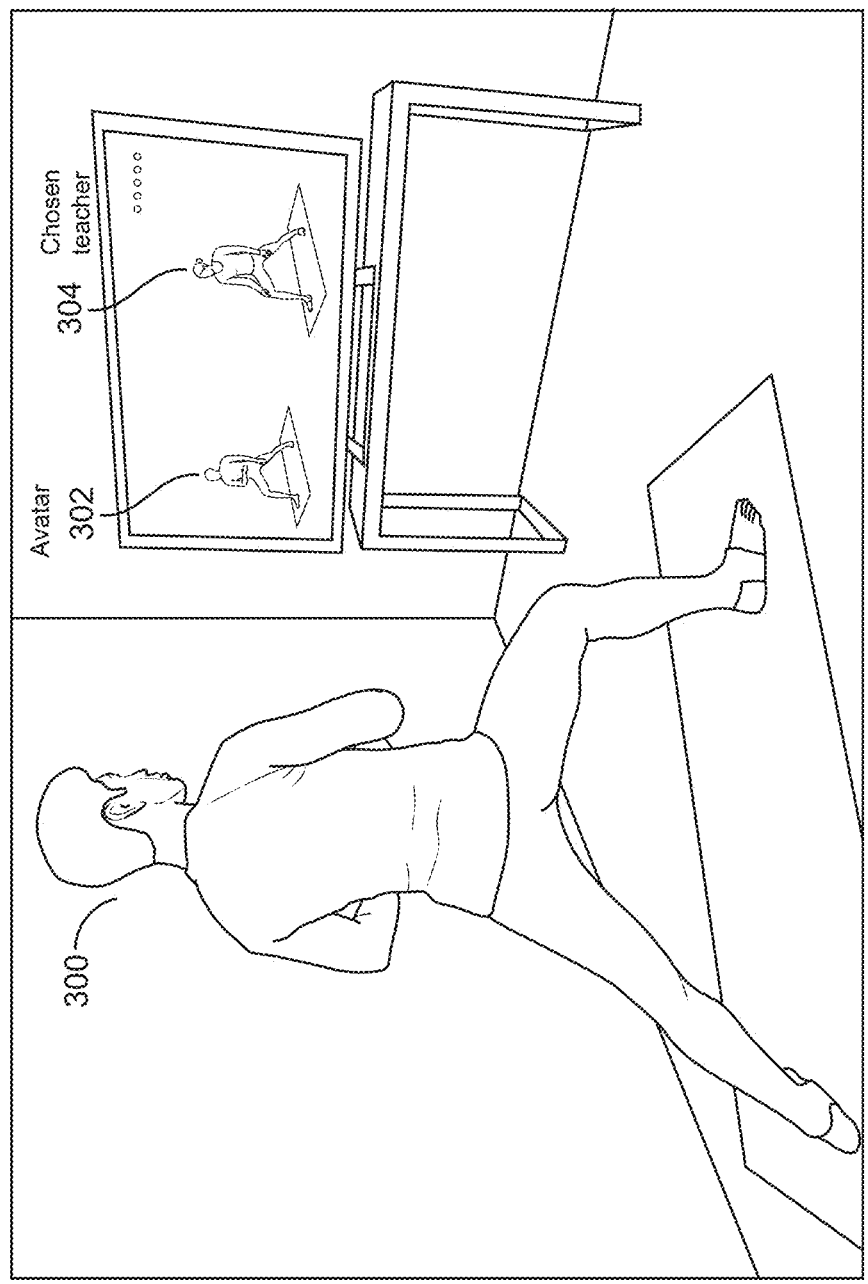
FIG. 3A shows an exemplary display a user may see, where a live avatar is rendered and inserted into a display video.

Referring now to FIG. 3A, it shows an exemplary display a user 300 may see a live avatar 302 is inserted into a display video. During the playback of an instructional video by a chosen teacher 304 in the PIVOT Yoga App, there are some extra spaces on one side of a frame. Into the extra space, the live avatar 302 representing the user 300 may be inserted as a comparison to the chosen teacher 304. For example, as the user raises his left arm, the corresponding avatar on the screen raises its left arm as well. In one embodiment, the avatar is rendered based on the sensor data received from the clothing embedded with the sensors. In another embodiment, one or more cameras are used to capture the pose of the user, images from the cameras are analyzed to derive a pose of the user, where the derived pose is used to render the avatar. As different camera angles come into view, the avatar, or appropriate portion of the avatar in the event of a close-up, will automatically move into correct position in view of the teacher.

Once in a pose, the user 300 may ask the system or strictly speaking, the chosen teacher for feedback on his pose. The request is received and recognized (nearly instantaneously), the view on the display may change. Instead of being in a side-by-side video environment, the user is now presented in an environment that has been specially designed for pose comparison. It is herein to refer this environment as Live Pose Comparison. According to one embodiment, the request may be generated from one or more sensors by the user tapping on a specific part of his body or a voice from the user.

In one embodiment, the avatar representing the user is superimposed on top of a reference avatar representing the teacher or a model designated by the teacher. Directly to the side is a numbered diagram of the mat, each side of the mat presents a perspective view of the avatar-teacher combination, and the user may switch among those views by calling out a selected view with his voice.

Figure 3B:
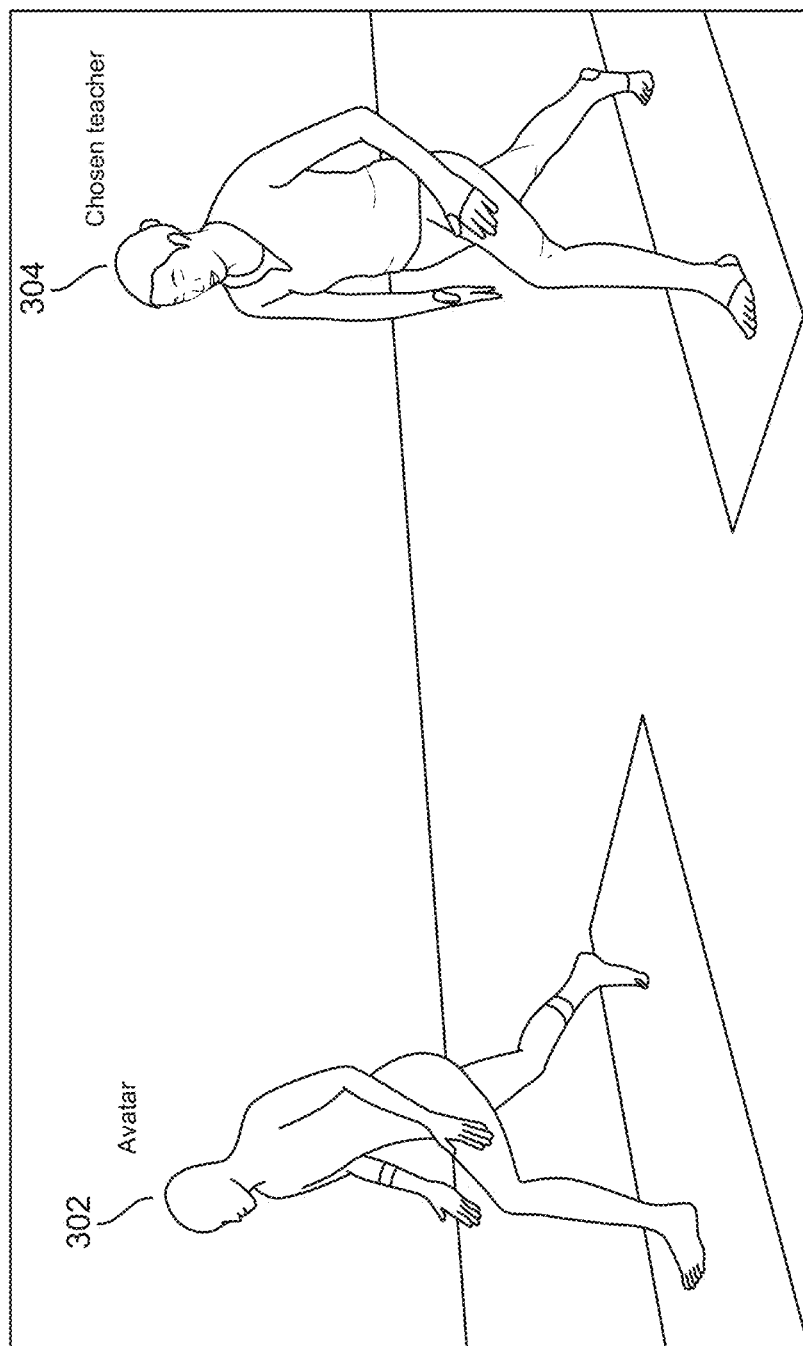
FIG. 3B shows an example of a perspective view (e.g., a 45-Degree view) in which a user avatar is placed on the right side of a representation of a chosen teacher.
Figure 3C:
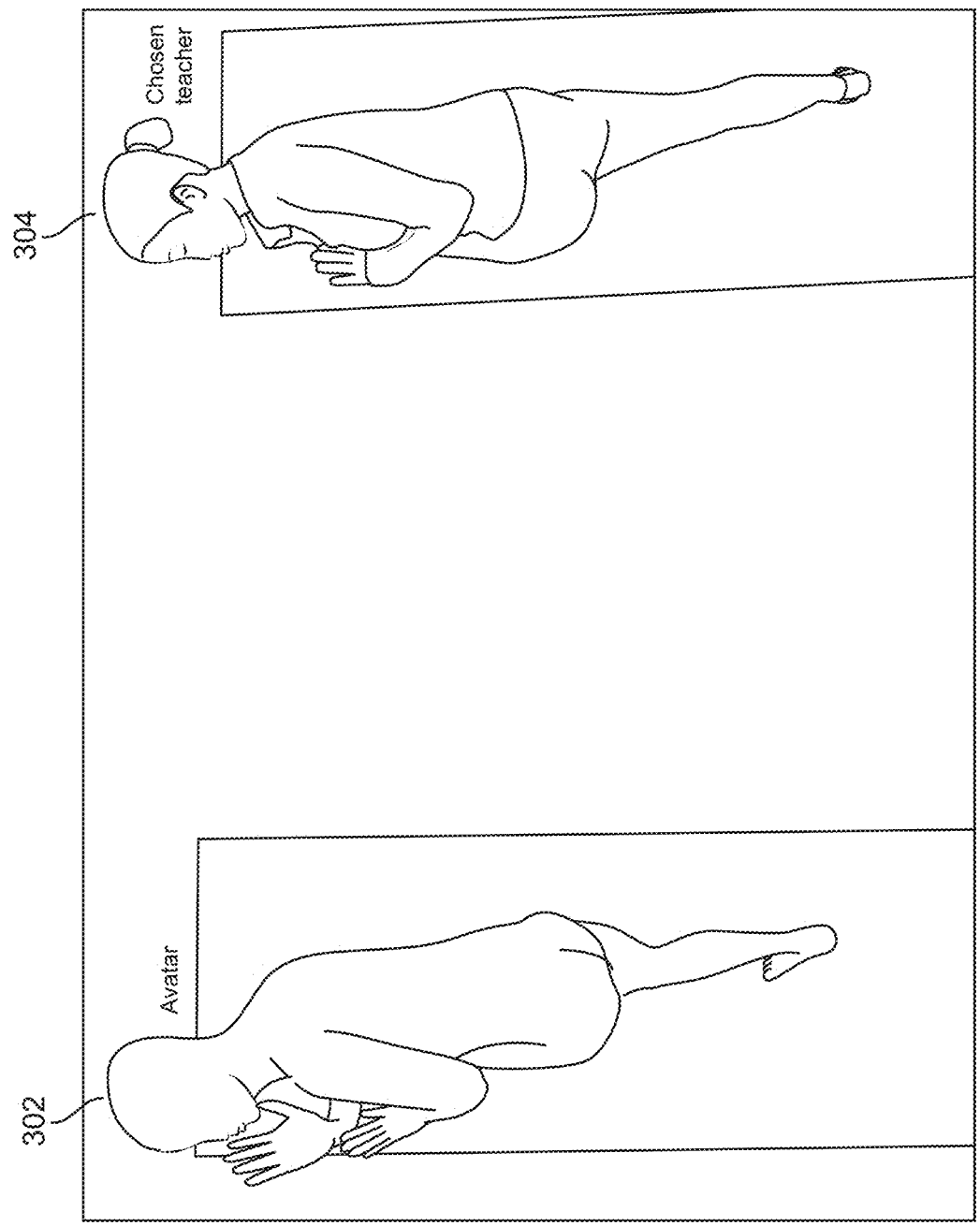
FIG. 3C shows an example of a direct overview, where a user avatar is placed on the left side of a representation of a chosen teacher.
Figure 3D:
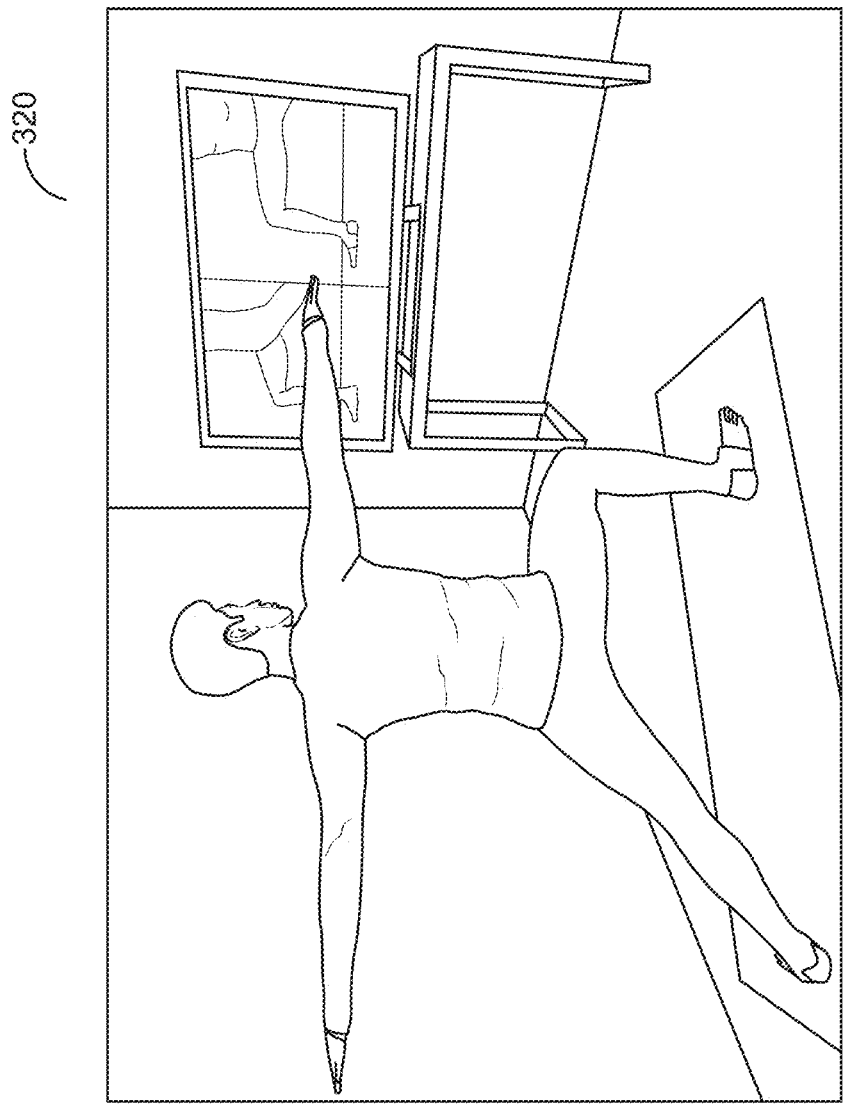
FIG. 3D shows a zoomed or close-up view of a user knee in a pose in comparison with the same performed by a chosen teacher, also in zoomed view.

FIG. 3B shows an example of a 45-Degree view, where the user avatar 302 is placed on the right side of the chosen teacher 304. FIG. 3C shows an example of a direct overview, where the user avatar 302 is placed on the left side of the chosen teacher 304. FIG. 3D shows a zoomed or close-up view 320 of a user knee in a pose in comparison with the same performed by the chosen teacher 304, also in zoomed view.

Figure 3E:
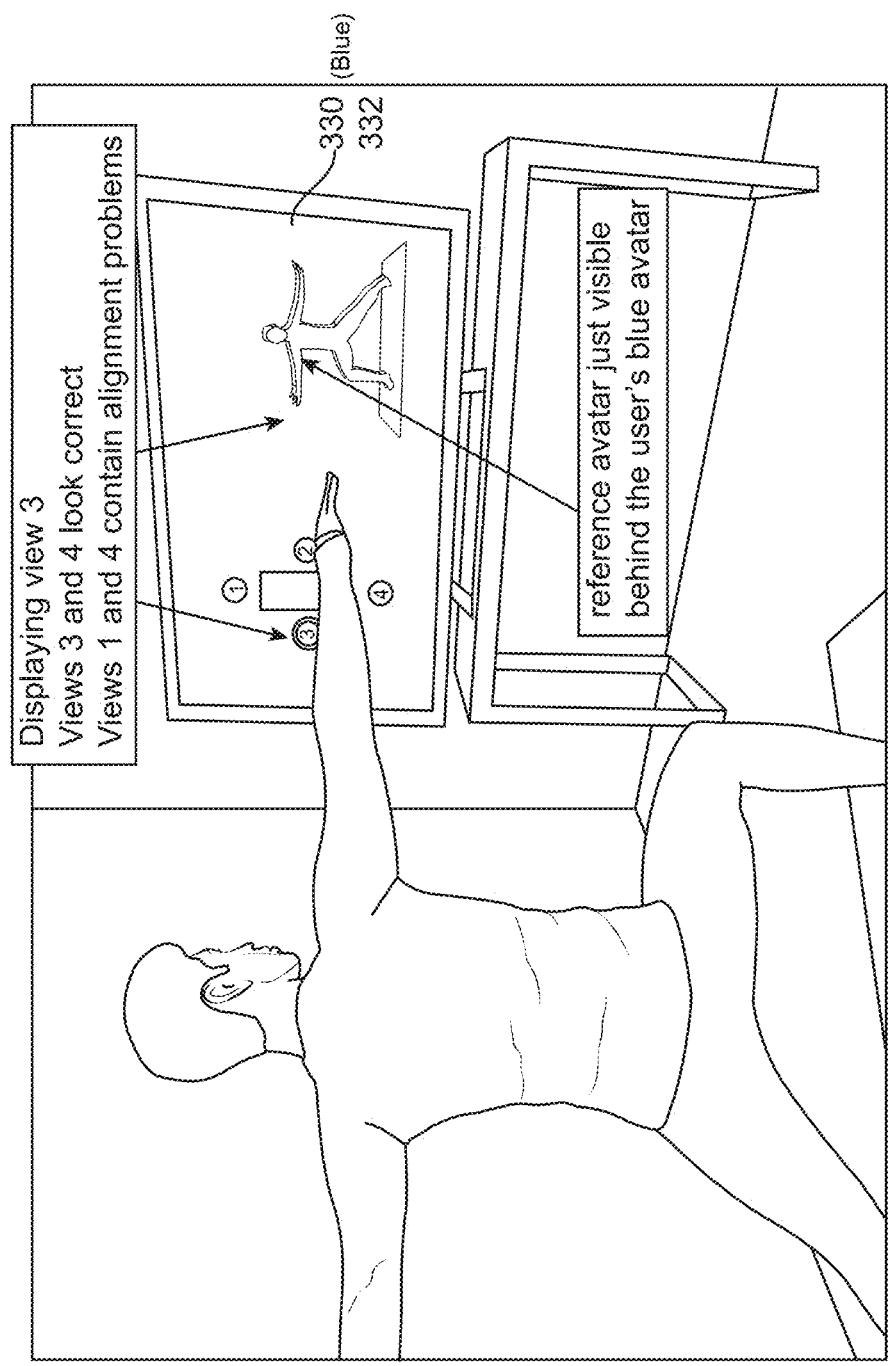
FIG. 3E shows what is referred to herein as Live Pose Comparison (LPC) Mode.

FIG. 3E shows what is referred to herein as Live Pose Comparison (LPC) Mode. Instead of being in a side-by-side video environment, the user is now presented in an environment that has been specially designed for pose comparison. In one embodiment, a user avatar 330 is superimposed directly on top of a reference avatar 332 (e.g., the teacher or a designated model by the teacher). Directly to the side is a numbered diagram of the mat, each side of the mat presents a different view of the avatar-teacher combination, and the user can switch among those views by calling out with his voice. According to one embodiment, as soon as the LPC is displayed, a teacher voice announces feedback in response to the pose the user is holding at the moment the user asked for feedback. This feedback may announce an important change that is needed at the moment and all done in the teacher voice. For example, the voice may indicate which body part needs to move, and how far in which direction.

Figure 3F:
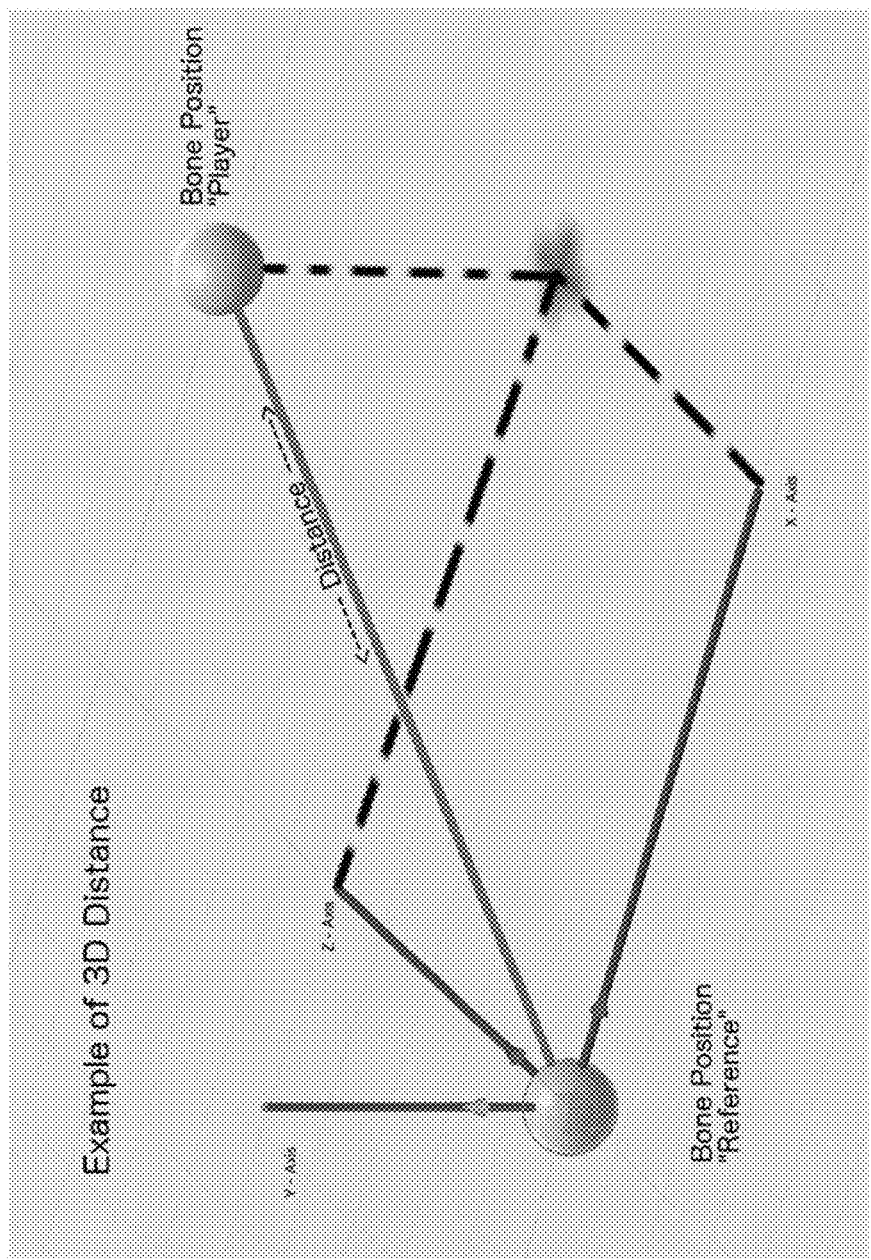
FIG. 3F shows the pose comparison by comparing the bones (or frames) of the user or player avatar to the bones (or frames) of the reference avatar.

In one embodiment, the pose comparison is done by comparing the bones (or frames) of the user or player avatar to the bones (or frames) of the reference avatar as shown in FIG. 3F. All of the bones are compared to their corresponding counterparts (e.g. the right hand of the player is compared to the right hand of the reference) using the basic 3D distance formula. This gives a distance between the current poses of the player and the reference. In one embodiment, the distance in Unity is measured in a predefined unit (e.g., meters or inches). The Unity is the 3D game engine software with which the system is designed.

With the results of this pose comparison, the player bone with the highest distance to its direct counterpart is identified. Errors between the two poses can then be determined. In one embodiment, an error is expressed in 3 component vectors (X/Y/Z), and a largest error component is to be corrected first. For example, if the bone with the largest error is the right knee, and the largest component of the error is −0.2 meters (negative corresponding to left) on the X Axis, then the player is instructed to move his right knee 0.2 meters to the right. This comparison is done in order and may be repeated if a threshold is not reached. In one embodiment, there is a default order. The player is instructed to correct his feet first, then his legs, chest, hands, and arms (in that order).

In addition to the pose correction, the decision about what body part to present for correction is a decision that can be made solely by the teacher. Each of the authoritative teachers adopted in the system may specify which errors in view of the pose differences to be corrected in any given pose, and a relative priority order of each of these corrections. In other words, different teachers may have different procedures to correct a pose error by a user (student). Accordingly, the selection of bones, the order in which they are corrected, and the axis that has priority for each bone, are determined and configured for each pose individually by a chosen teacher.

Regardless it is generic or teacher-specific pose correction, one of the important features is that the system (e.g., PIVOT Yoga) provides automatic confirmation of a user's adjustment to a correction. In one embodiment, as soon as the user had made the suggested correction (within a pre-set tolerance level), the App is designed to have a response from the teacher, e.g., "That's good!" or "Please move your right arm a bit more right".

In the LPC mode, the user avatar is superimposed onto the teacher avatar (normalized so that the heights of the two avatars are substantially similar or the same), and the user has the control for changing which side of his yoga mat is being displayed. If there are significant-enough alignment problems on a particular side of a pose, that corresponding view is highlighted (e.g., in red). The assessment is based on a tolerance level that may be predefined or set up by a user or the teacher.

A user may always rely on the avatar comparisons directly. The reference avatar can be in a different color (e.g., yellow) and visually behind the user avatar as shown in FIG. 3E, any yellow peeking through would generally indicate an alignment error for the user pose. Even though the user avatar and reference avatar are displayed in 2-dimension (2D) planes, the raw avatar data (bones and joint angles) are being tracked and compared in full 3-dimension (3D) space accuracy. More viewing angles in any 2D views (e.g., top view) and any 3D views (e.g., rotating in 360 or 720 degrees) can be provided and shown.

As an extension to the pose comparison, for each bone on the player, the axis with the highest degree of error is identified and counted. The axis is used to determine which angle would give the player the best view of his avatar for correcting his pose error. For example, if there are 10 bones, the user receives correction messages 5X, 3Y, and 2Z. In this scenario, the user has the most errors in the X Axis (left/right), so top-down or frontal view may be selected based on other refining factors.

For the teacher-specific pose comparison, the system is designed to automatically display to the user the camera view for the side of his pose which has the most severe alignment problems according to the chosen teacher. Based on the teacher's prioritized bone order of correction, the camera angle is selected based on the prioritized bone's largest error in the X, Y, or Z axis.

According to one embodiment, a user scoring algorithm is designed. For each pose, there is a 3D reference model (e.g., based on or from the teacher). Based on the model, it can be calculated how closely the user is approaching that pose in 3D. The difference may be reported, for example, as a percentage. According to one embodiment, each frame is observed while the user is nominally in a given pose. The frame that has the smallest percentage of overall deviation against the reference pose is selected with full 3D accuracy. The percentage is recorded as a score for that pose in the teacher's sequence on that day, and can be used to track the pose (and display it to the user) over time. An underlying scoring algorithm is to leverage the pose comparison. For each bone on the player, the distance to its direct counterpart is saved. These distances are compared against a set of thresholds to determine the score. For example, if the minimum threshold is 0.05 meters, the maximum threshold is 0.25 meters, and all bones are greater than 0.25 meters from their counterparts, then the player would receive a score of 0 (zero). Likewise, if the bones were all less than 0.05 meters from their counterparts, the player would receive a score of 100 (one-hundred). Values on this scale are determined by how far each bone is from its counterpart.

Figure 3G:
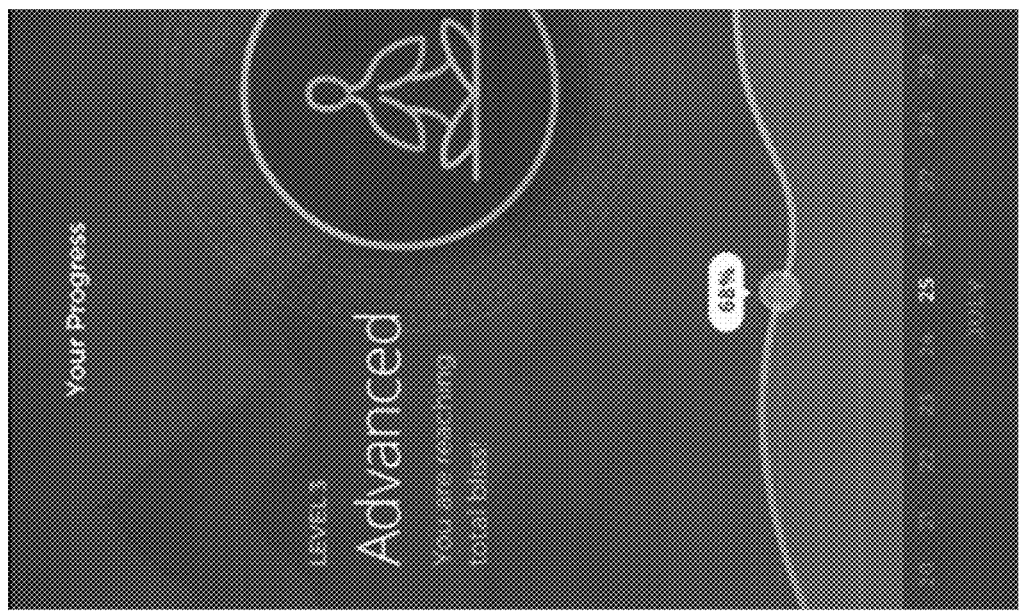
FIG. 3G shows an exemplary score chart.

For a second example, if there are 10 bones, 8 of which are below the minimum threshold, and 2 of which are beyond the maximum threshold, then the player would receive a score of 80%. FIG. 3G shows an example of scoring of poses performed by a player over a period, which also shows the score statistics of the player for each pose or aggregated poses of each session, tracking the progress over time and multiple sessions. The App presents this scoring to show the user his "Best" or "Worst" pose, and enable the user to share each on a social media, e.g., Facebook.

Figure 3H:
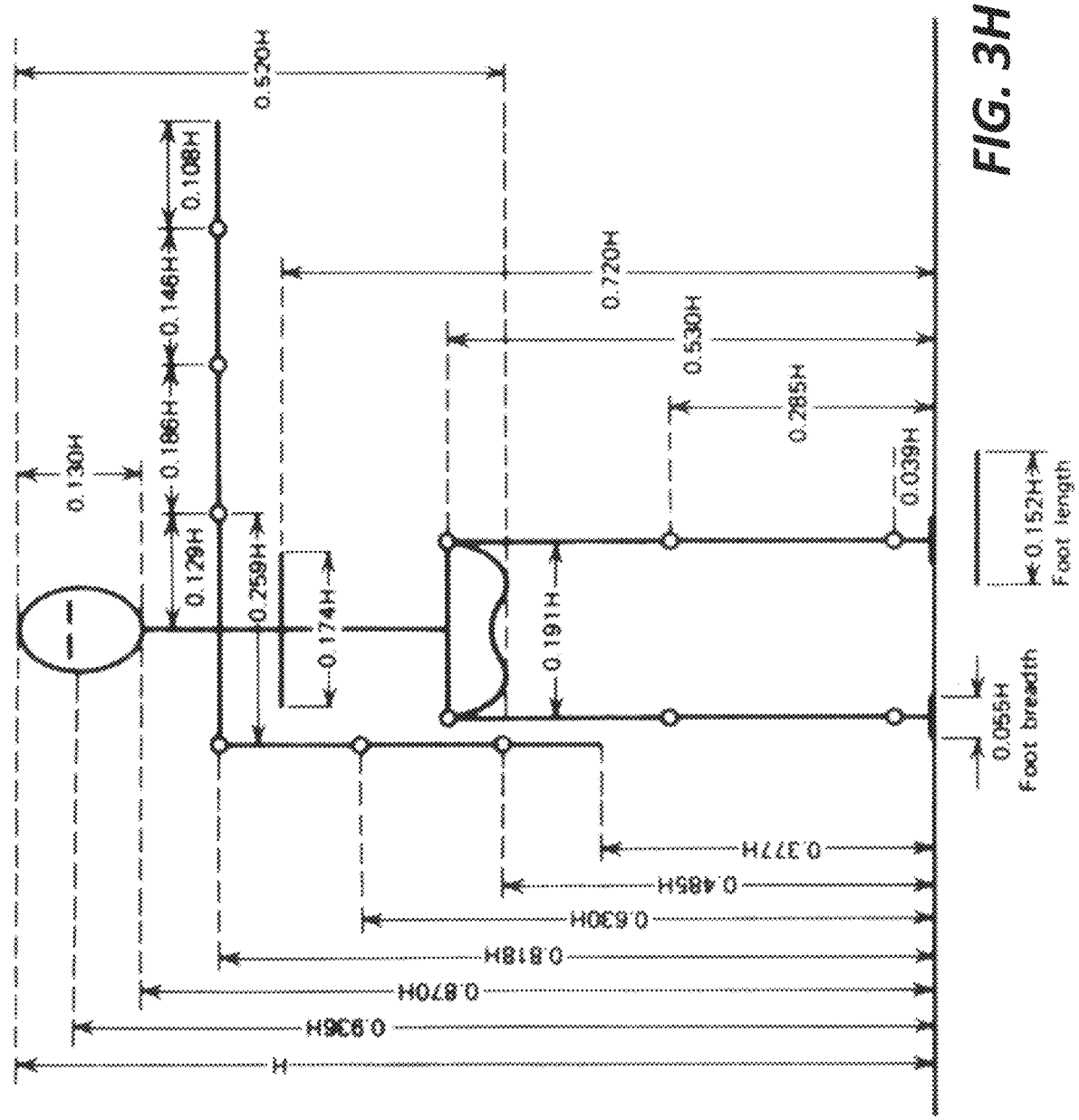
FIG. 3H shows that the length of all body segments can be approximated as a ratio of user height (H)

To give more realistic animation, the user avatar is modeled as accurately as possible. In one embodiment, a user height is obtained from the user. The height information is used for all calculations, especially for modeling the user avatar when to place the avatar on the screen (e.g., where to place on the screen the head of the user who is bending at his knees). The standard anthropometric parameters are used, where the length of all body segments can be approximated as a ratio of user height (H) as shown in FIG. 3H. This approximation may differ in certain actual body segment length(s) of the user. In one embodiment, the user's actual body part lengths are adopted to scale the user avatar body parts, through initial calibration poses that could be actual yoga poses.

There are times, particularly in Yoga, certain poses have well known positions in which known body parts must be on the ground and at certain joint angles. For example, the Downward Facing Dog pose has both hands and feet on the ground (mat) with the legs, spine and arms fairly straight. If a user is asked to be in this pose, and yet the user avatar's hands or feet are not planted on the ground/mat, certain body segment length(s) are scaled accordingly to match user's actual pose with hands and feet on the mat. To reduce variation of the pose, markings (e.g., hand prints, foot prints) on the mat are used to position the user according to his height. So based on stored knowledge of which poses require which, the length of the avatar's bones can be mathematically expanded or contracted. In general, a user can be asked to do multiple "calibration" poses to arrive to the best body segment scaling of the avatar specific to the user.

Figure 3I:
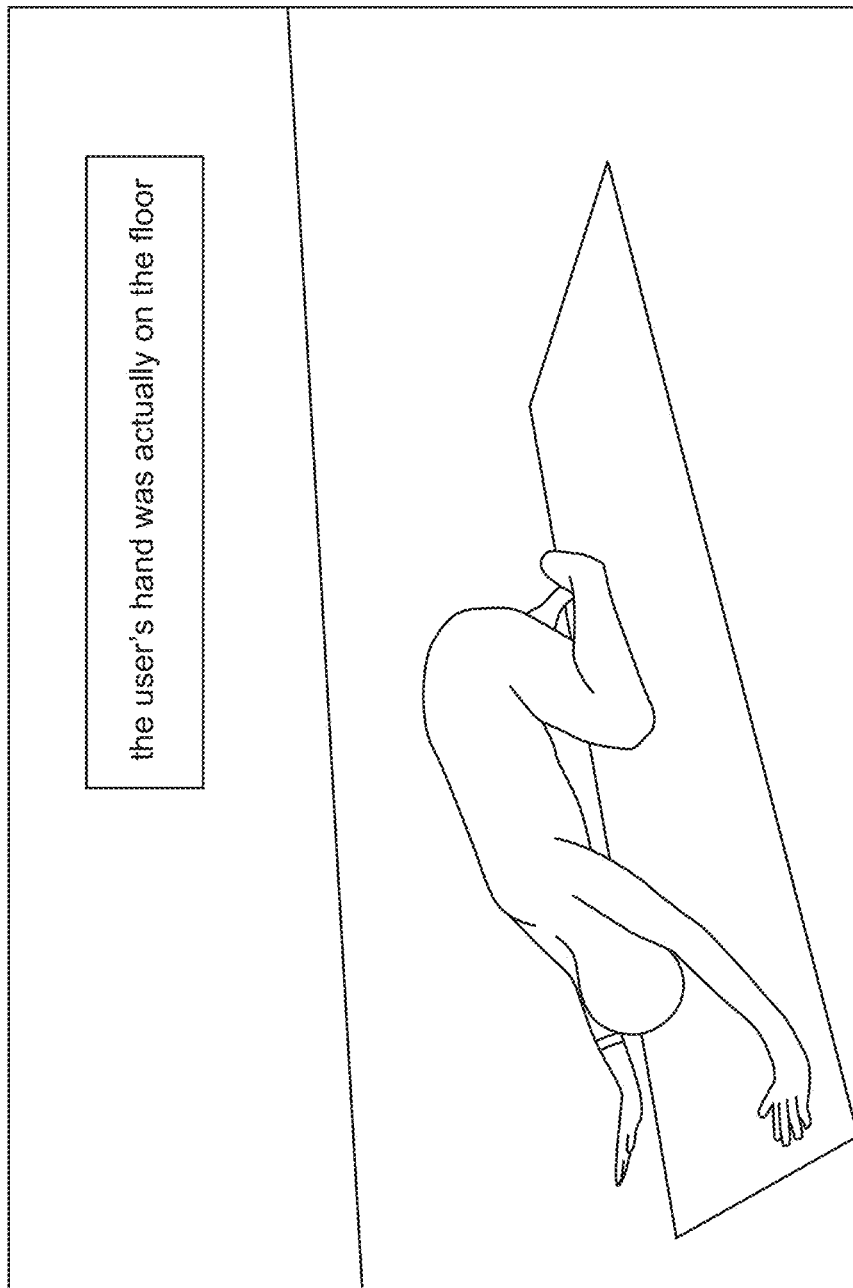
FIG. 3I shows an example in which a user's hand is not rendered to touch the floor.

Many calculations are made in real time to display all parts of a user's body properly. All of those calculations require an anchor which is a single point that all measurements are based from. It turns out that using the same anchor for all poses can create some small discrepancies. After all, some poses in yoga are standing up; and some poses are lying down; and some poses are on the hands and knees. If the user is in a pose with their hands on the floor, and we're using an anchor that assumed the user was standing up, the result will be that the user's hands, in the motion capture display, would not actually seem to touch the floor, as shown in FIG. 3I.

To address this, dynamic anchoring technique is designed to chooses an anchor point in the background based on a known pose. In one embodiment, the dynamic anchoring method ensures that any given avatar always remains on the 'ground' in 3D space (in Unity). This is achieved by identifying which bone on the avatar has the lowest position on the Y Axis, and moving the entire avatar by the opposite of that value such that the lowest bone is always at ground level.

Figure 4A:
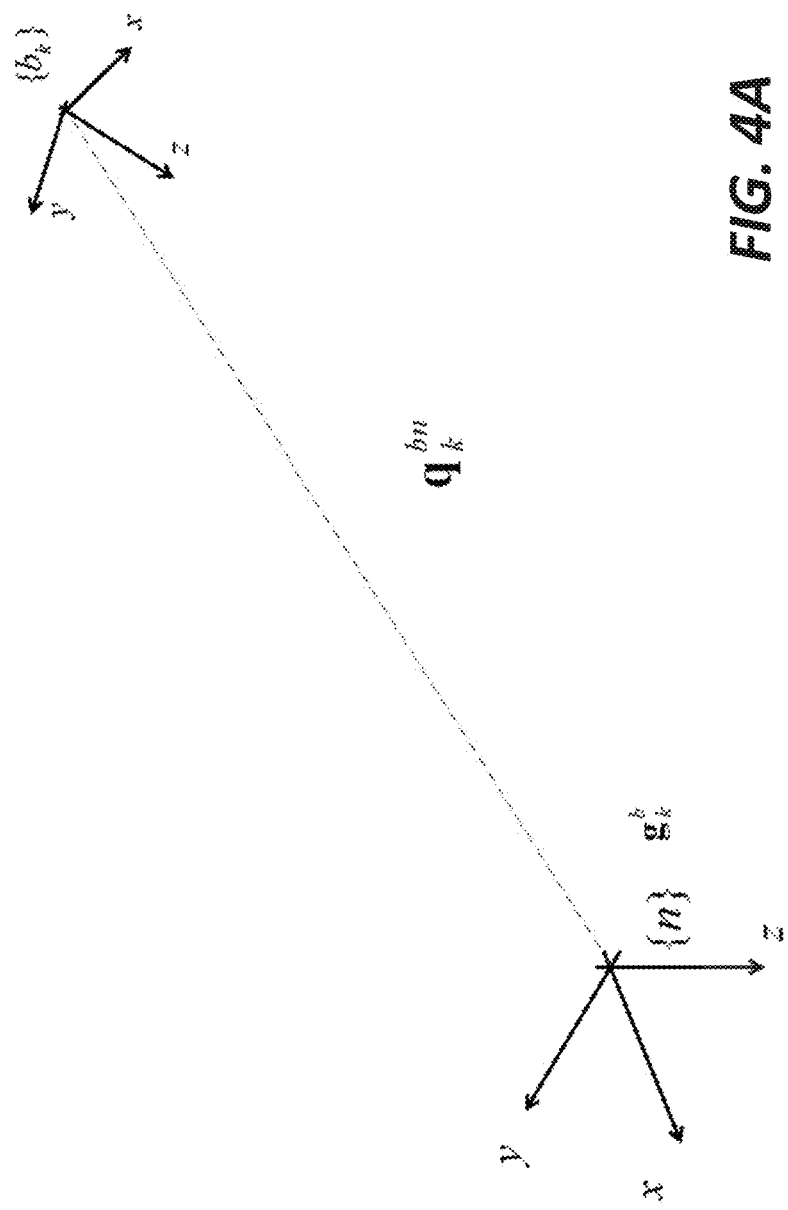
FIG. 4A illustrates a quaternion of orientation $q_k^{bn}$ which rotates the global reference frame {n} into the sensor (local) reference frame {b} at time k.

According to one embodiment, a motion capture system (referred herein as PIVOT Mag Free) is designed and relies on gyroscope and accelerometer only. The inertial sensors in FIG. 1B are 6-axis inertial sensors having only gyroscopes and accelerometers. The design is based on an algorithm for tilt estimation (angles with respect to the vertical direction) which is augmented with gyroscope integration for the heading estimation (angle about the vertical direction). A sensor fusion algorithm is designed to take the accelerometer and gyroscope measurements as an input. The output is the quaternion of orientation $q_k^{bn}$ which rotates the global reference frame {n} into the sensor (local) reference frame {b} at time k, see FIG. 4A. The global reference frame of the sensor fusion algorithms running in each sensor has the z axis aligned with the vertical direction and the x and y axis (in the horizontal plane) resulting from the initial sensor orientation.

Figure 4B:
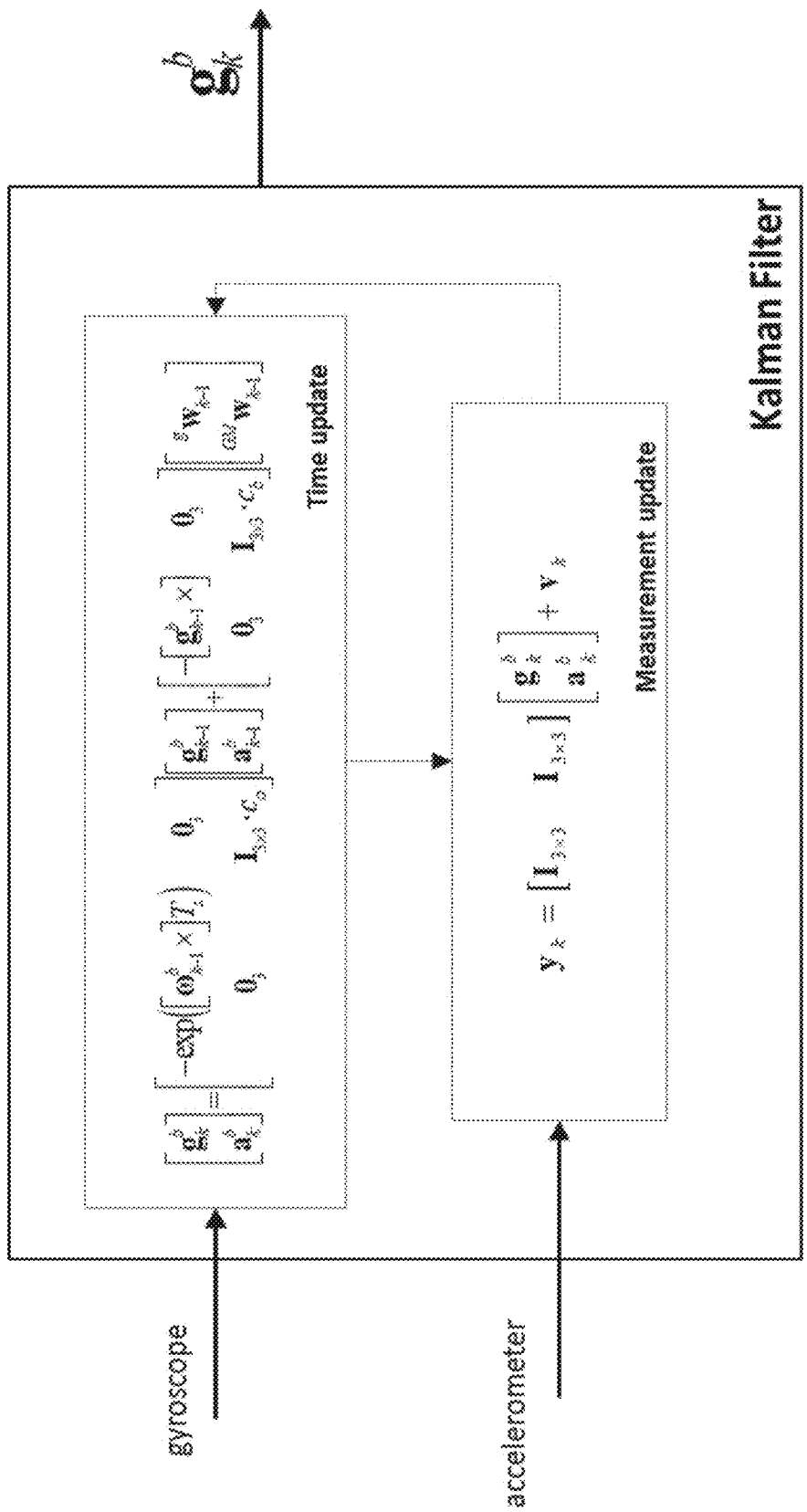
FIG. 4B shows an algorithm block diagram implementing a linear Kalman filter to estimate the vertical direction in dynamic conditions by means of the gyroscope and accelerometer data.

In one embodiment, a linear Kalman filter is used in order to estimate the vertical direction in dynamic conditions by means of the gyroscope and accelerometer data. The algorithm block diagram is presented in FIG. 4B. After the vertical direction is estimated, a horizontal reference needs to be available in order to compute the tree dimensional orientation of the sensor reference frame with respect to the global reference frame. Since a magnetometer is not used in PIVOT Mag Free, this horizontal direction can be computed with the gyroscope data. At time zero, the horizontal reference measured in the body frame is assumed to be a known canonical vector, i.e., the x axis (1, 0, 0) of the global reference frame. As the time passes and the body moves, the gyroscope data is used to project in time the horizontal reference in the body reference frame. The time-propagation equation of a 3D vector, given the body angular velocities, is given by the following equation:

$$\begin{cases} h_0^b = (1, 0, 0) \\ h_{k+1}^b = -\exp([\omega_k^b]T_s)h_k^b \end{cases}$$

Figure 4C:
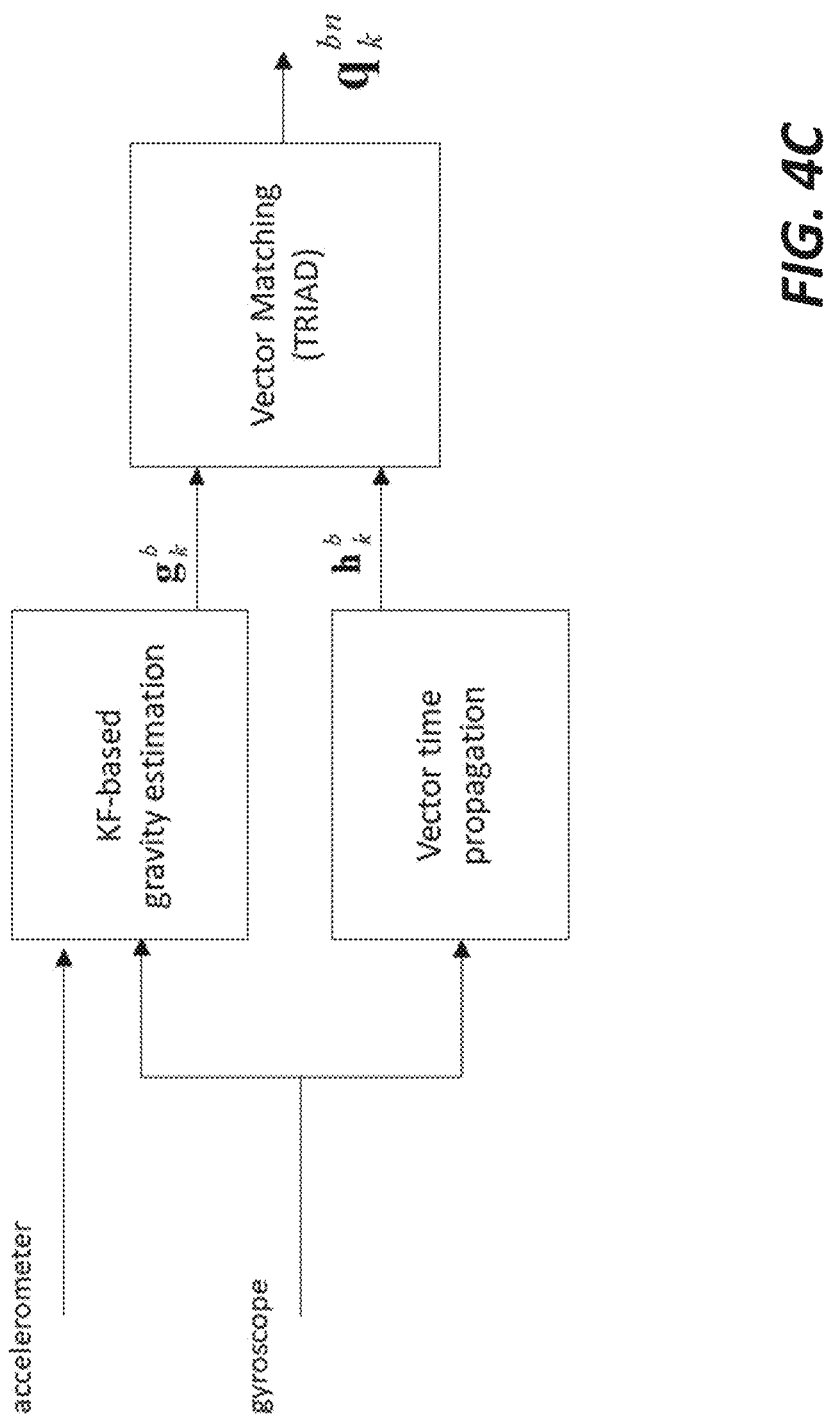
FIG. 4C shows an overall workflow of the three-dimensional orientation estimator according to one embodiment.

Once the horizontal and vertical directions are known in the global reference frame (known a priori) and in the sensor reference frame (estimated with sensor data), the orientation of the global reference frame with respect to the sensor reference frame can be computed. In one embodiment, the TRIAD method being a very popular computational procedure is used. FIG. 4C shows an overall workflow of the three-dimensional orientation estimator according to one embodiment.

A non-null bias in the gyro measurements sometimes results in a drifting error in the output of the angular speed time integration. Such a bias can be accurately estimated by averaging gyroscope measurements while the sensors are still (e.g., on a table). However, the accuracy of the estimated bias is heavily degraded by possible user motions during the calibration procedure. For this reason, the Kalman filter is designed for being able to estimate the gyroscope biases while the sensors are worn by the user. The rationale is to use a more complex algorithm (a Kalman filter vs. a simple average) to deal with user's (moderate to low) motion during the gyroscope calibration.

In one embodiment, the gyroscope measurements $gyr_k^b$ are modeled as the sum of the true angular velocity $\omega_k^b$, the gyroscope bias $b_k^b$ and the white noise $v_k^b$:

$$gyr_k^b = \omega_k^b + b_k^b + v_k^b$$

Figure 4D:
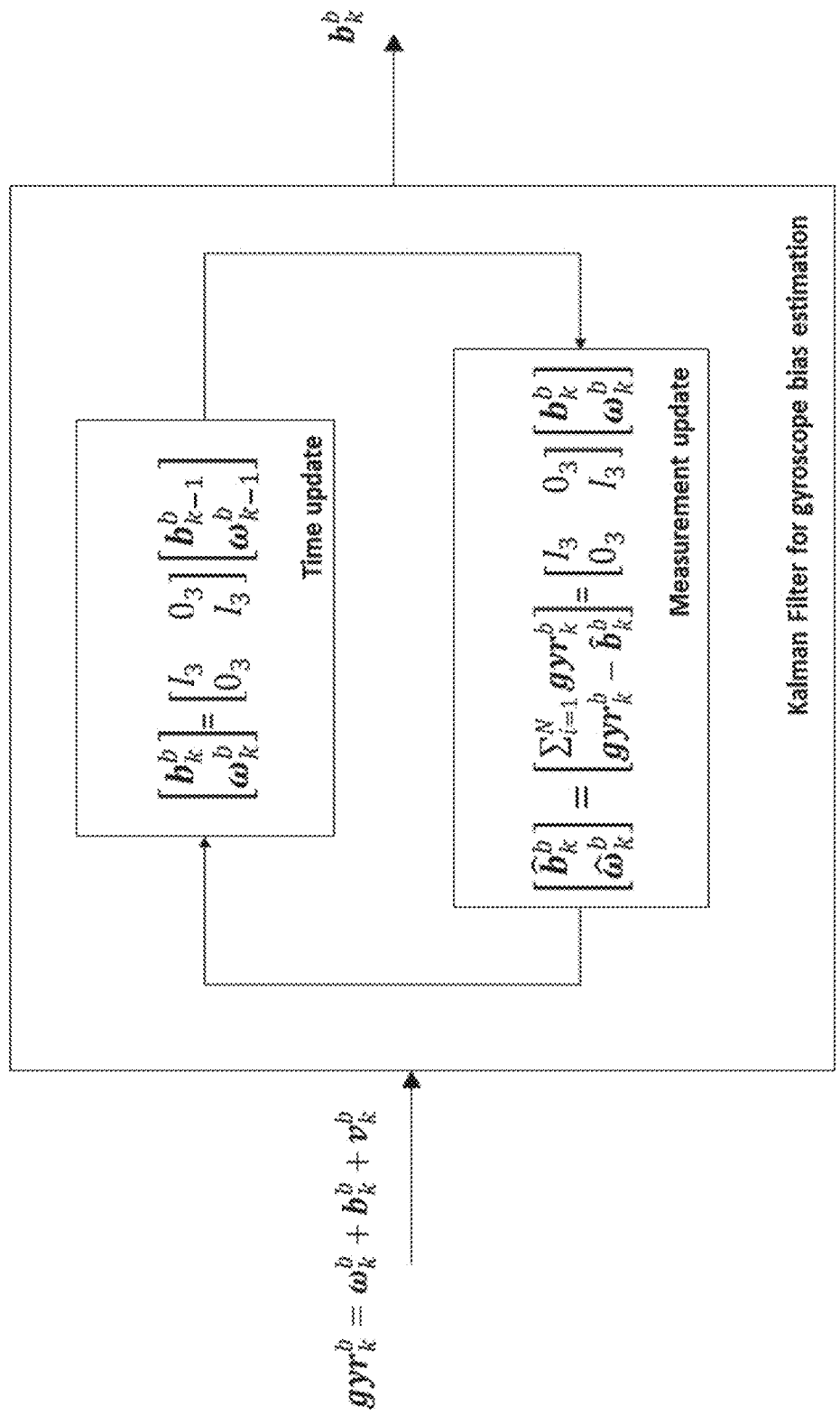
FIG. 4D shows the estimation of the bias $b_k^b$ given the measurements $gyr_k^b$.

The aim of the Kalman filter in PIVOT Mag Free is the estimation of the bias $b_k^b$ given the measurements $gyr_k^b$, as shown in FIG. 4D. The bias and the angular velocity are considered as the inner state of a dynamical system. These two states are modeled as time-constant variable. These states are also considered to be the output of the dynamical system, as shown in FIG. 4D. They can be derived from the gyroscope measurements as follows:

$$\begin{cases} \hat{b}_k^b = \sum_{i=1}^{N} gyr_k^b \\ \hat{\omega}_k^b = gyr_k^b - \hat{b}_k^b \end{cases}$$

A biomechanical protocol implemented in PIVOT Mag Free includes a set of definitions and computational procedures that allow relating sensor readings (angular velocity and acceleration) and sensor fusion output (quaternions) to the motion of the body segment. Three main blocks are required to reach this goal: the biomechanical model definition, the Sensor-To-Segment (STS) calibration and the alignment of the global reference frames of each sensor attached to the body.

Biomechanical Model

Figure 4E:
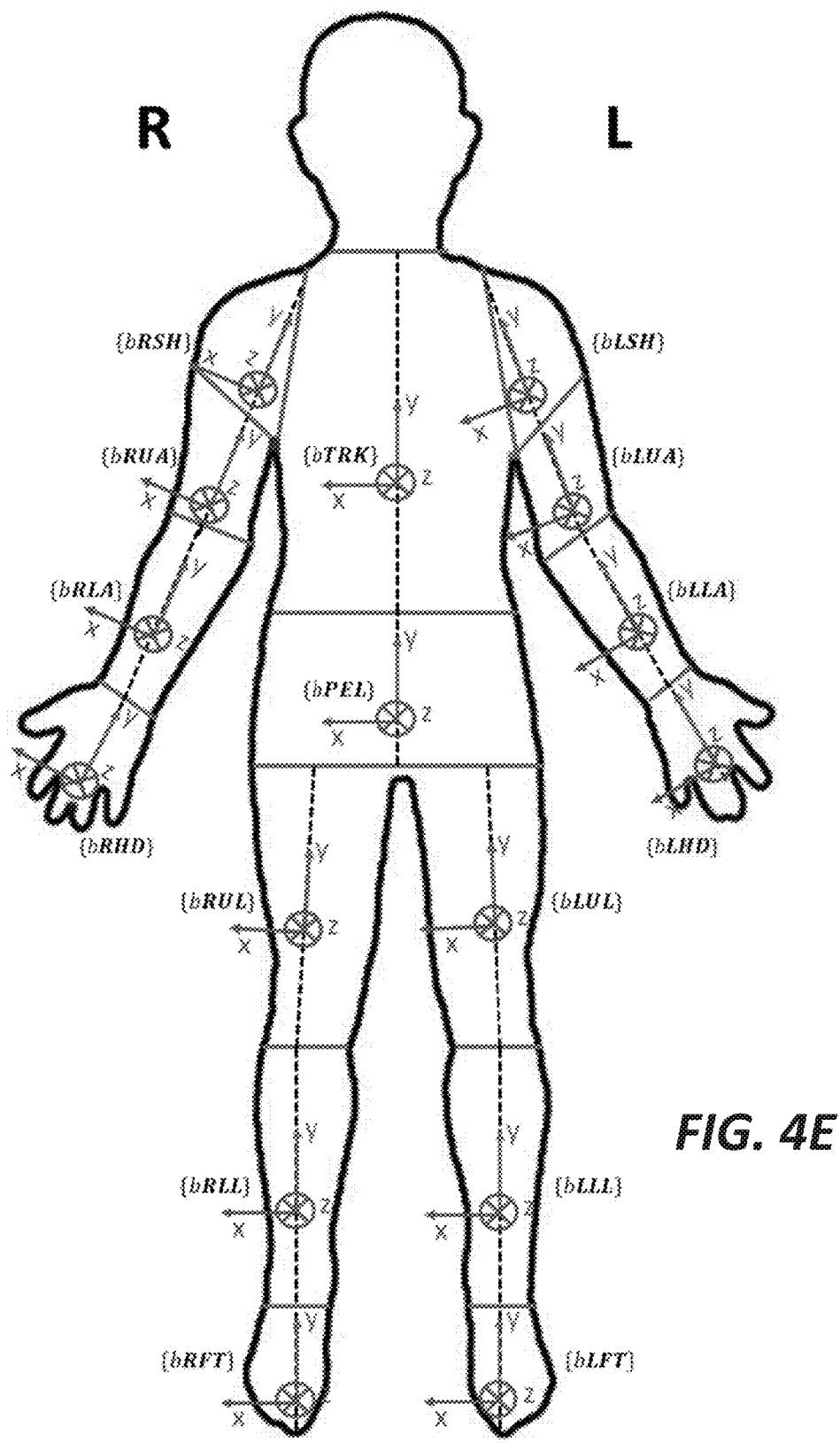
FIG. 4E illustrates an exemplary biomechanical model defined in the PIVOT Mag Free biomechanical protocol according to one embodiment of the present invention.

The biomechanical model defined in the PIVOT Mag Free biomechanical protocol is shown in FIG. 4E according to one embodiment of the present invention. Specifically, FIG. 4E shows an anatomical reference frame for all of the 16 body segments considered in PIVOT Mag Free. The y-axis is assumed to be the longitudinal axis for all the body segments while the x-axis is assumed to coincide with the medio-lateral direction (positive from left to right). Therefore, the z-axis is represented by the antero-posterior direction (positive from the front to the back). In one embodiment, fourteen body segments are considered: six segments for the upper limb: upper arm, forearm and hand (left and right), six segments for the lower limb: thigh, shank and foot (left and right), trunk and pelvis.

Sensor-to-Segment Calibration

It is known to those skilled in the art that there are two main approaches: anatomical methods, where a user is asked to stay still in simple and known body poses (N-pose, T-pose and etc.) and functional methods, where the user is asked to perform very simple calibration motions. In the former, the estimated quaternions are compared with the ones expected in the known static pose. From this comparison, the STS misalignment (STS quaternion) is estimated with the aim of compensating the IMUs quaternions during the motion capture session, where IMU stands for inertial measurement unit, each IMU is included in a sensor module. In the latter, body rotational axes are measured through the calibration motion in the sensor reference frame and then used to build the STS orientation.

As described above, the quaternions returned by PIVOT Mag-Free sensor fusion running for each body segment refer to a different global reference frame. In one embodiment, a functional method (two-step procedure) is used to estimate the STS quaternion based on the raw sensor data, i.e. accelerometer and gyroscope data.

Vertical Direction Estimation: N-Pose

The first step of the proposed calibration method includes asking a user to stay still in N-pose. For each sensor, accelerometer data is measured and averaged during this time window to produce an estimate of the reaction to the gravity (vertical direction, upward) seen from the sensor reference frame. The N-pose assumption derives that each body segment reference frame has the y-axis (see FIG. 4E and FIG. 4F) which is aligned with the vertical direction. For this reason, the averaged accelerometer vector represents an estimate of the longitudinal direction of the relative anatomical reference frame.

Medio-Lateral Direction Estimation: Functional Motions

Figure 4F:
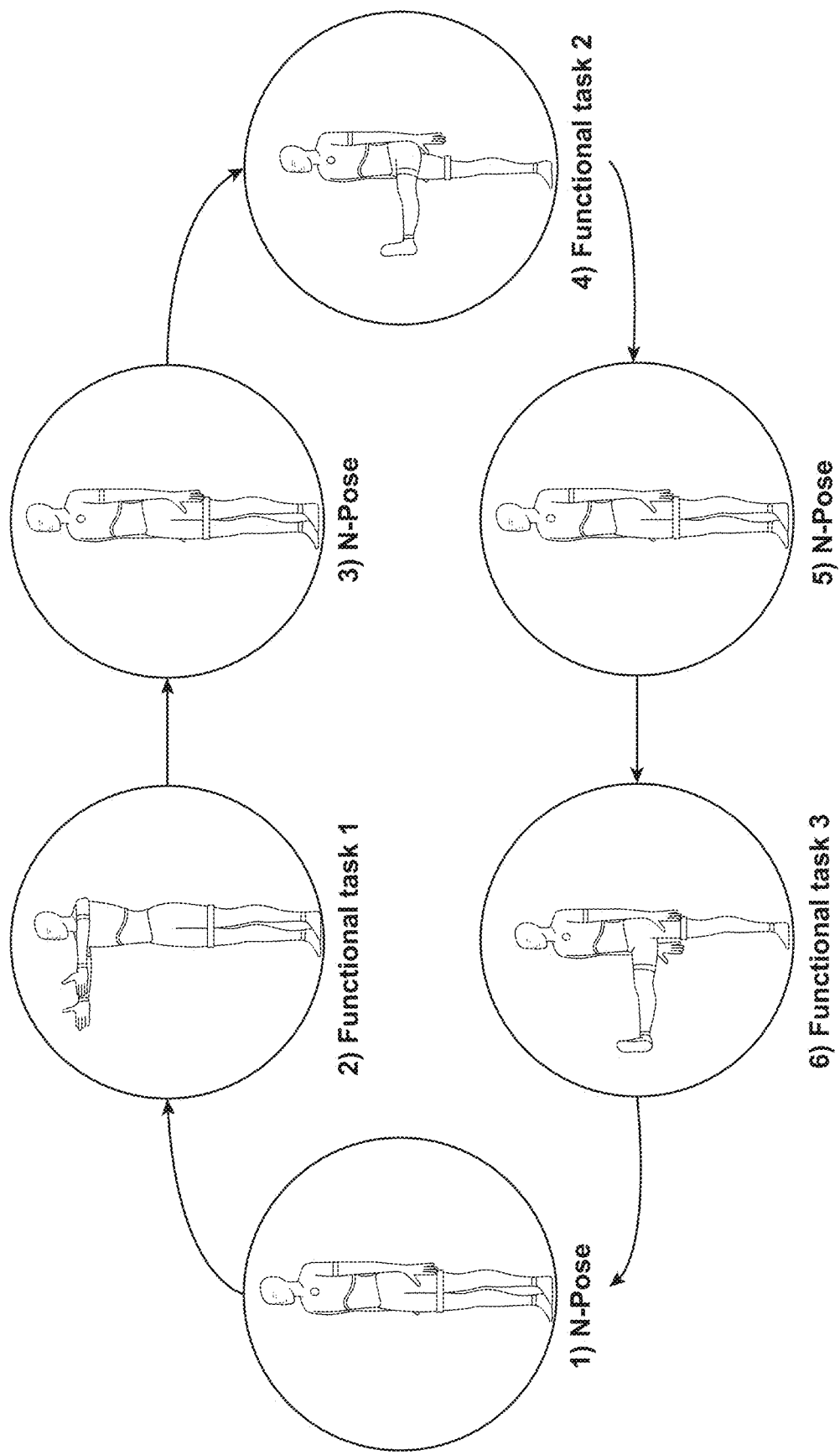
FIG. 4F shows that an N-pose assumption derives that each body segment reference frame has the y-axis.

The second step of the STS calibration implemented in PIVOT Mag Free is represented by the functional motions. In this stage, the user, starting from an N-pose, is asked to perform the following motion sequence as shown in FIG. 4F:

90 degrees flection of the upper arms in the sagittal plane, keeping the forearm and hand rigid with respect to the upper arms.

90 degrees flection of the left thigh in the sagittal plane, keeping the shank and the foot rigid with respect to the thigh; and 90 degrees flection of the right thigh in the sagittal plane, keeping the shank and the foot rigid with respect to the thigh.

During each motion, gyroscope measurements are acquired and normalized to one. The circular average of the normalized gyroscope represents the estimate of the Medio-lateral direction of that body segment seen from the corresponding sensor reference frame. No functional motions are required for the trunk and pelvis because sensor position on those body segments is quite constrained by the garment design. Therefore, the medio-lateral direction is assigned a-priori according to the physical orientation of the sensor with respect to the body.

Medio-Lateral Direction Refinement: Angular Grid-Search Method

The medio-lateral direction estimated during the functional motions described above can have a poor inter-subject repeatability. This is especially true for those body segments with relevant amount of soft tissues and muscles such as the upper arms and the thighs. For this reason, in PIVOT Mag Free a computational procedure was introduced which is called angular grid-search. The underlying idea of this method is to consider the output of the functional motions output (i.e. the average mean of the gyroscope data) as an initial guess which is then refined based on the computation of a cost function over a pool of candidate directions. In the following, the main steps of the grid-search algorithm are listed and detailed.

Angular Grid Computation

Figure 4G:
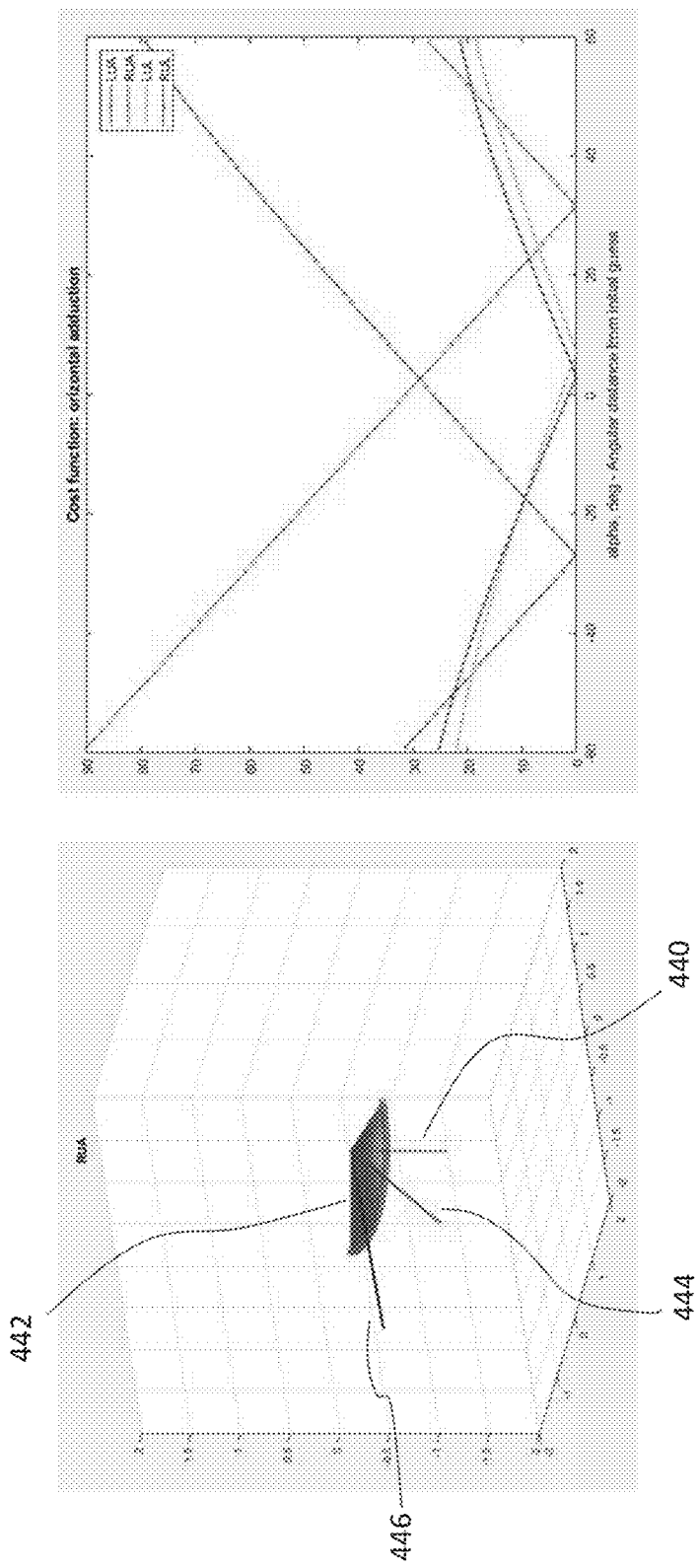
FIG. 4G shows (a) a grid search algorithm working principle for one body segment, angular grid, anatomical longitudinal axis, mediolateral direction initial guess and refined mediolateral direction (black), and (b) a cost function over the grid for four body segments left and right upper arm and left and right upper leg.

The angular grid is represented by a pool of directions which lie in the horizontal plane and are equally distributed in the range of +/−60 degrees with respect the initial guess. The horizontal plane is computed as the plane orthogonal to the vertical direction estimated during the first N-pose by means of the accelerometer data. In FIG. 4G, the line 440 represents the vertical direction while the lines 442 represent the guess directions. Such grid is built by computing all the directions in the horizontal plane with an increment of about 1.5 degrees, spanning the +/−60 degrees range with respect to the initial guess. The initial guess is represented by the projection onto the horizontal plane of the average gyroscope vector computed during the functional motions (the line 444). The refined (and final) direction is represented by the line 446.

Cost Function Computation

The cost function is based on the assumptions that functional motions are performed within the sagittal plane with null pronation. Hence, for the arm segments (upper arms, forearms and hands) the cost function to be minimized is represented by the horizontal adduction during the arm functional calibration (stage 2 in FIG. 4F). Same rule is applied to the leg segments, considering the corresponding functional calibration stage. The direction which results in the cost function minimum is taken as the medio lateral direction for that segment. As an example, in FIG. 4G, the cost function for the left upper arm, right upper arm, left upper leg and right upper leg are reported.

Final STS Orientation Estimation: TRIAD Method

From the biomechanical model definition, the vertical and medio-lateral directions of all body segments are assigned as (0, 1, 0) and (1, 0, 0) respectively. On the other hand, both directions have been measured in the two-step procedure described above. Therefore, given this coupled vector observations, the STS orientation can be computed easily by means of the TRIAD method.

Global Reference Frame Alignment

Figure 4H:
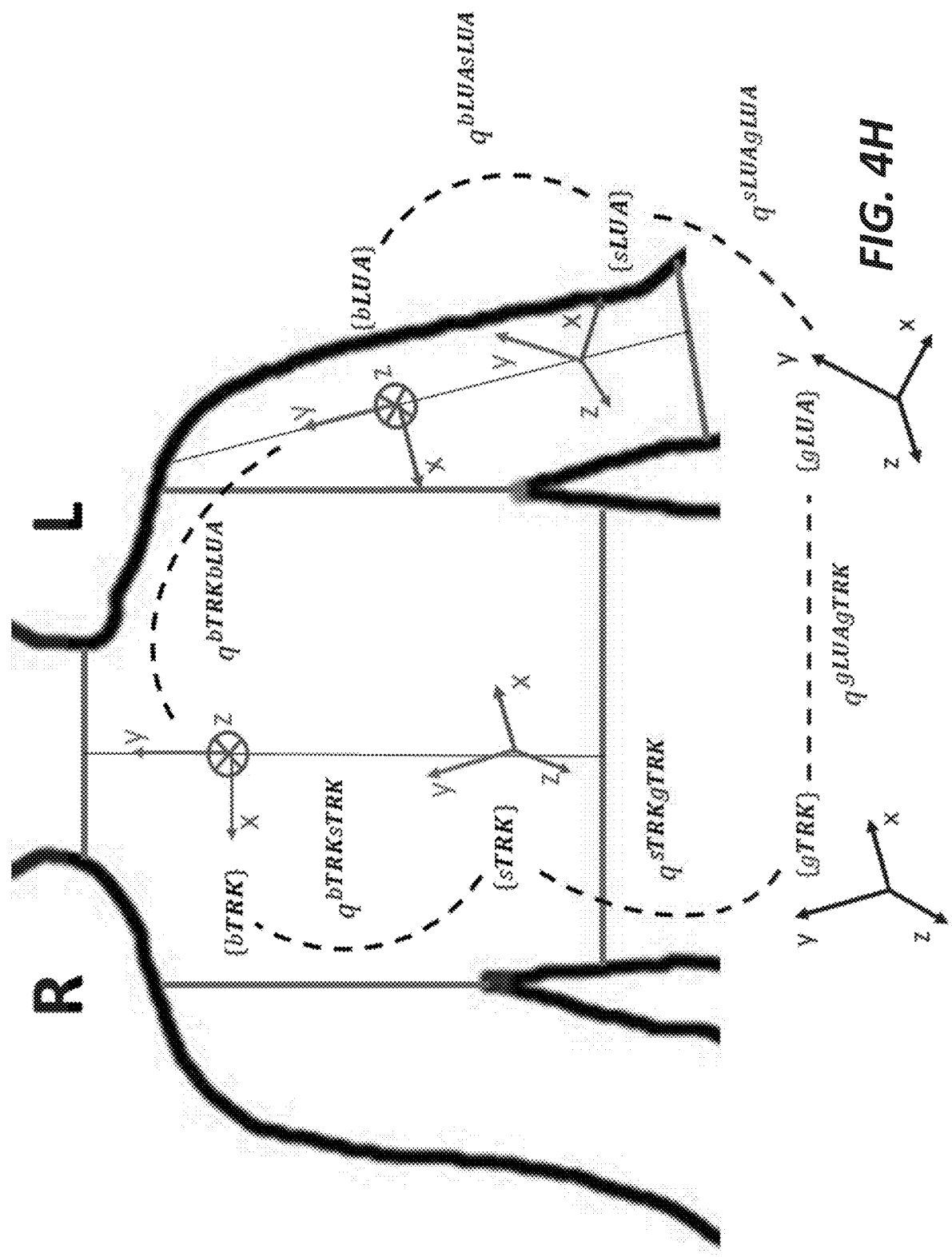
FIG. 4H shows each IMU has a global reference frame that depends on its physical orientation at the time in which a sensor fusion algorithm is started.

Each IMU has a global reference frame that depends on its physical orientation at the time in which the sensor fusion algorithm is started, as shown in FIG. 4H. Hence, a further compensation is needed when joint angles are to be computed. It should be noted that this additional step would not be required by standard sensor fusion algorithms that make use of magnetometer measurements. In fact, it is possible to define a unique global reference frame for all the sensors when magnetometer data are used. For this reason, an additional computational stage is added in the PIVOT Mag Free biomechanical protocol workflow. This procedure needs to be repeated every time a new motion capture session is started (i.e. all the sensor fusion algorithms are started on all the body segments). Two assumptions are necessary: the user is in an N-pose and STS calibration quaternions are already available.

For example, considering the trunk and the right upper arm, the following equation holds:

$$q^{gRUAgTRK} = (q^{sRUAgRUA})^{-1} \otimes (q^{bRUAsRUA})^{-1} \otimes q^{bRUAbTRK} \otimes q^{bTRKsTRK} \otimes q^{sTRKgTRK}$$

If assumption 1 hold, then $q^{bRUAbTRK}=(1,0,0,0)$, since the trunk and right upper arm body segments are aligned during N-Pose:

$$q^{gRUAgTRK} = (q^{sRUAgRUA}|_{Npose})^{-1} \otimes (q^{bRUAsRUA})^{-1} \otimes q^{bTRKsTRK} \otimes q^{sTRKgTRK}|_{Npose}$$

If assumption 2 holds, then $q^{bRUAsRUA}$ and $q^{bTRKsTRK}$ are known and the global reference frame misalignment $q^{gRUAgTRK}$ can be computed.

In PIVOT Mag Free, the trunk is taken as the global reference. Therefore, the generic formula to estimate the global reference frame misalignments between the reference (trunk) and any other body segment X can be computed as follows:

$$q^{gXgTRK} = (q^{sXgX}|_{Npose})^{-1} \otimes (q^{bXsX})^{-1} \otimes q^{bTRKsTRK} \otimes q^{sTRKgTRK}|_{Npose}$$

It shall be noted that this estimated global reference misalignment will hold for all the motion capture sessions, but it needs to be recomputed if the sensor fusion algorithms are restarted.

The joint orientation computation between two body segments is computed with the following formula:

$$q^{bDISbPRX} = q^{bDISsDIS} \otimes q^{sDISgDIS} \otimes q^{gDISgTRK} \otimes (q^{gPRXgTRK})^{-1} \otimes (q^{sPRXgPRX})^{-1} \otimes (q^{bPRXsPRX})^{-1}$$

where DIS stands for distal and PRX stand for proximal. This formula represents the way all the blocks described above (i.e., sensor fusion outputs, sensor to segment calibration and global alignments) are put together to estimate the joint orientations. It is also shown how the trunk global reference frame is taken as reference for all the other segments. The joint quaternion will then be transformed into joint angles with standard quaternion to Euler angles formula.

Figure 4I:
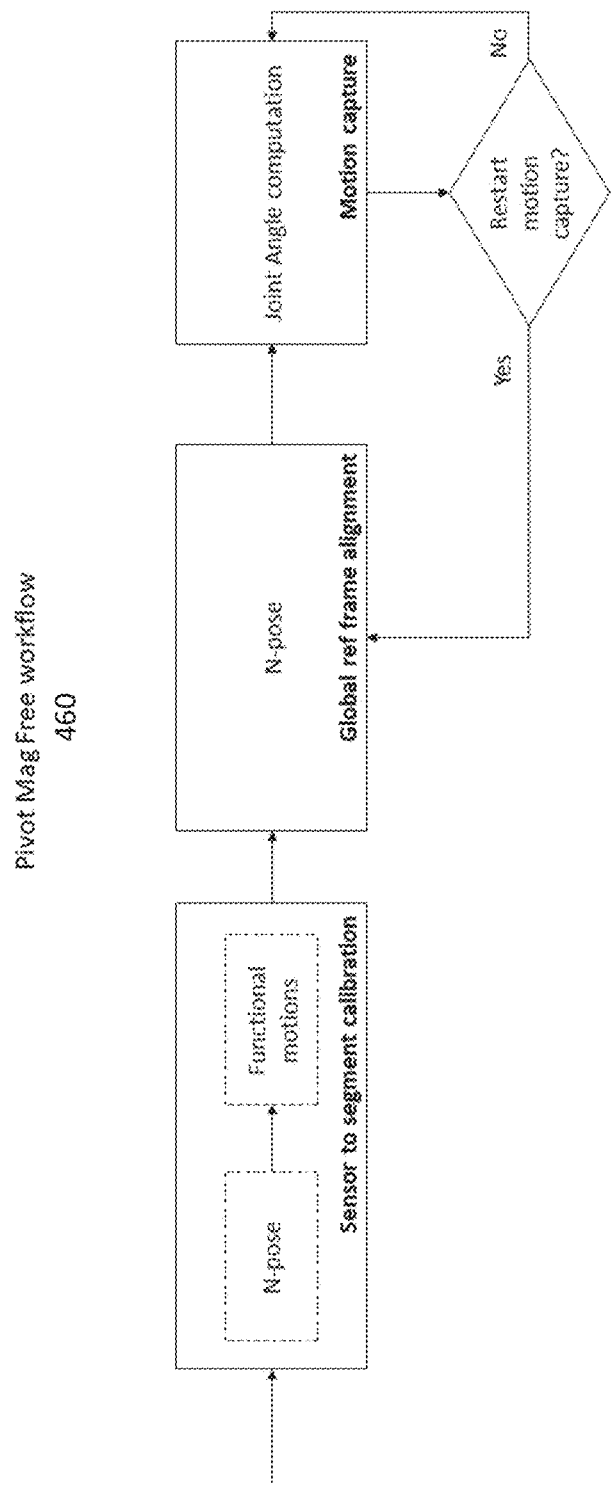
FIG. 4I shows a flowchart or process implemented in PIVOT Mag Free biomechanical protocol.

FIG. 4I shows a flowchart or process 460 implemented in PIVOT Mag Free biomechanical protocol. The very first phase is represented by the STS calibration, which consists in the first N-pose plus the functional motions. Then, to start a new motion capture session, sensor fusion algorithms are started. Since the user is supposed to stay in N-pose, it is possible to compute the global reference frame alignment described above. After that is accomplished, the real motion capture can start, with the joint angles computation as described in the formula above. Every time that the motion capture needs to be restarted, the user needs to go back to the global alignment stage to recompute the global reference frame alignment.

As the background application scenario involves the chance of an orientation drift, the yoga poses detection and classification algorithm must rely on measures unaffected by such errors. In one embodiment, a yoga pose is approximated with a quasi-static condition lasting for more than a second, it is then possible to exploit accelerometers data to compute body segments' attitude, thus inferring user's current pose in real time. A detection algorithm, also referred to herein as TuringSense Pose Detection Algorithm (TSPDA) is composed by the following sub-components or steps:

1) a model of each pose is detected, the model can be based on unprocessed accelerometers data or attitude angles, where the model may also comprise specific tolerance bounds for every body segment;
2) an algorithm capable of detecting user's absence of significant motion over a pre-defined time window in real-time;
3) an algorithm capable of extracting body-segments attitude angles from raw accelerometers' data, when the user is classified as 'still' or 'not moving' by the algorithm mentioned in (2);
4) a classifier capable of comparing body-segments attitude angles computed in (3) with the pose-models mentioned in (1), the classifier identifies in real time if the user is assuming one of the poses defined in the model databased (1). Even if no pose is detected, the classifier will detect a pose closer to the user's body configuration. The classifier is designed to be capable of improving the classification using the current 3D joint angles computed by the Mag Free algorithm;
5) a specific scoring system to provide the feedback on how much the user was close to the pose detected on (4), where the scoring system algorithm provides:
   a bounded (i.e., 0%-100%) score describing the overall user ability to match the reference pose
   a bounded (i.e., 0%-100%) score describing, for every body segment, the user's ability to match the reference pose.

Every pose to be detected will be modelled and described, based on the data collected with the TS Mag-Free system, in terms of: body segments attitude, body segments-specific attitude tolerances, body segments raw accelerations, body segments-specific raw accelerations tolerances, 3D joint angles, and joint-specific 3d joint angles tolerances and statistical weights.

Figure 5A:
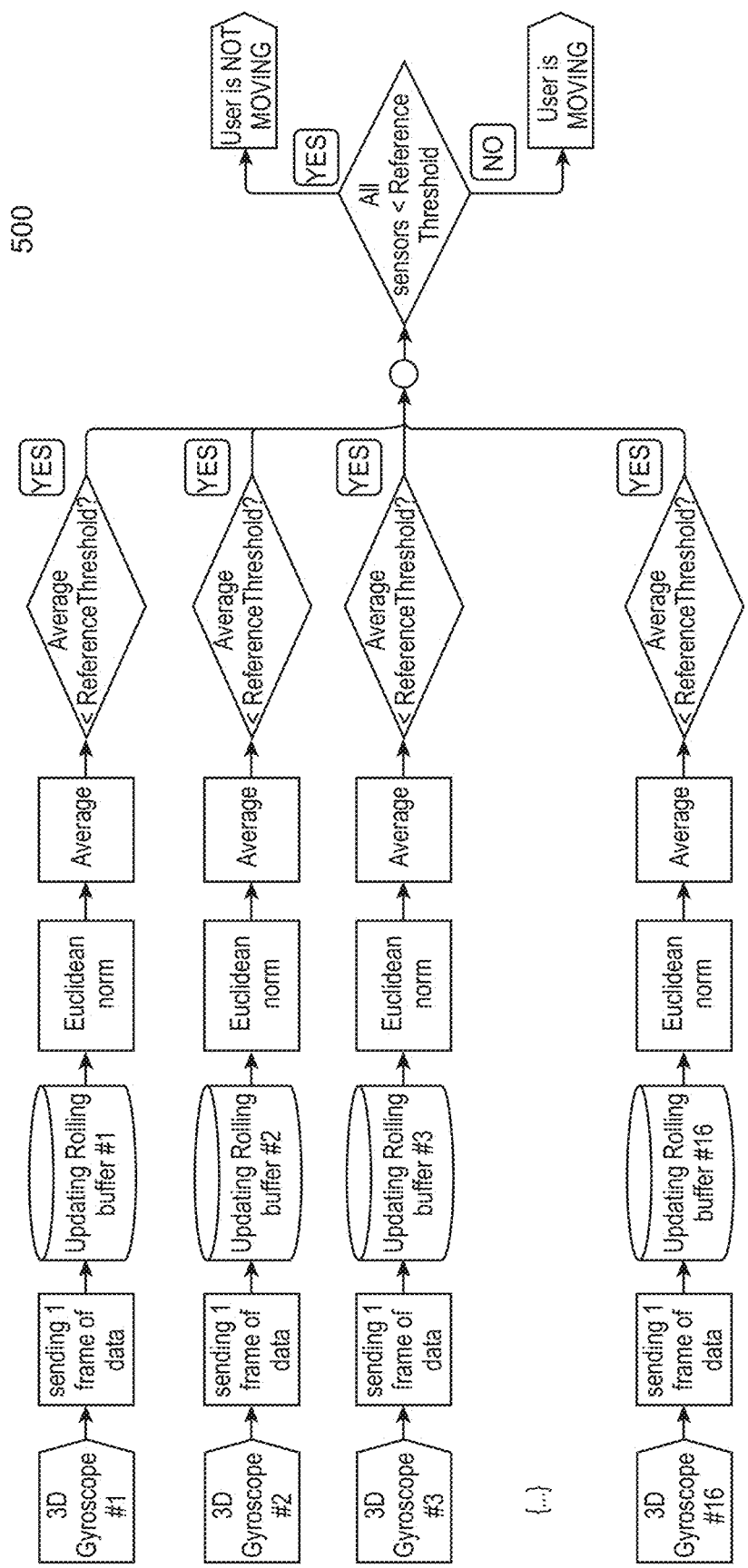
FIG. 5A shows a flowchart or process of detecting stillness (no motion) in a user.

An algorithm, also referred to as Body-Motion Detection Algorithm, is designed to collect and update in real time a rolling buffer of gyroscopes' data; the length of such buffer is pre-defined (e.g. 1 second), but can be changed at any time during the recording. Data is collected from the sensors placed on or near designated body segments of a user. Once the analysis buffer is filled (e.g. after the first second of recording), gyroscopes data is postprocessed, averaged and compared against pre-defined thresholds. If the current postprocessed and averaged gyroscopes data coming from all involved body segments is found lower than the pre-defined thresholds, the user's state shall be classified as "not moving". Only if the user's state is classified as "not-moving", the pose detection and classification will proceed further with the above steps (3) (4) and (5). FIG. 5A shows a flowchart or process 500 of detecting stillness (no motion) in a user.

An algorithm, also referred to as Body Segments' Attitude Estimation Algorithm, is designed to collect and update in real time a rolling accelerometers data buffer of a pre-defined length (i.e. 1 second). The data is collected from the Sensors placed on all user's body segments involved by the TS Mag Free protocol. In the same fashion, if already present, 3D joint angles data can be collected as well to improve the classification. Once the analysis buffer is filled (i.e. after the first second of recording), accelerometers data will be postprocessed and averaged.

Figure 5B:
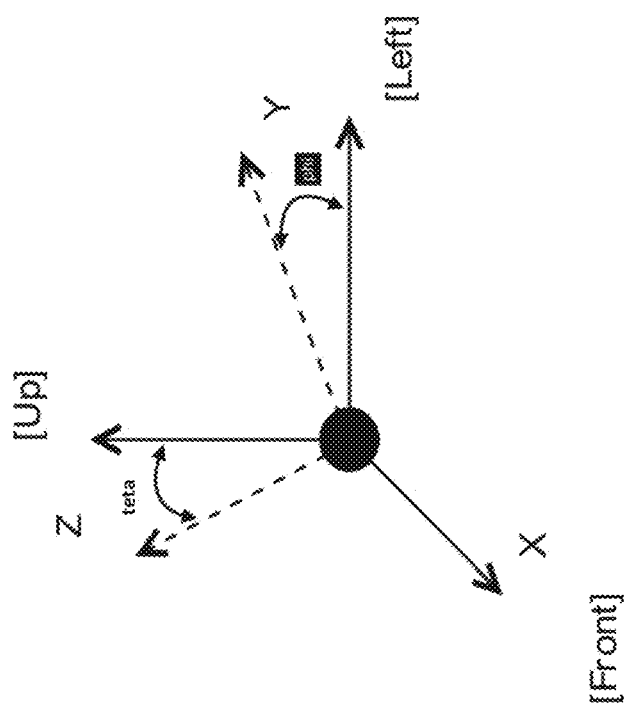
FIG. 5B shows the computations of attitude angles (phi, teta) for each body segment.

Knowing the sensors orientation a-priori, accelerations can be expressed in the body-segment system of reference, the attitude angles (phi, teta) for each body segment are computed as shown in FIG. 5B:

$$phi = atan\left(\frac{a_x}{\sqrt{a_y^2 + a_z^2}}\right)$$

$$teta = atan\left(\frac{a_y}{\sqrt{a_x^2 + a_z^2}}\right)$$

Figure 5C:
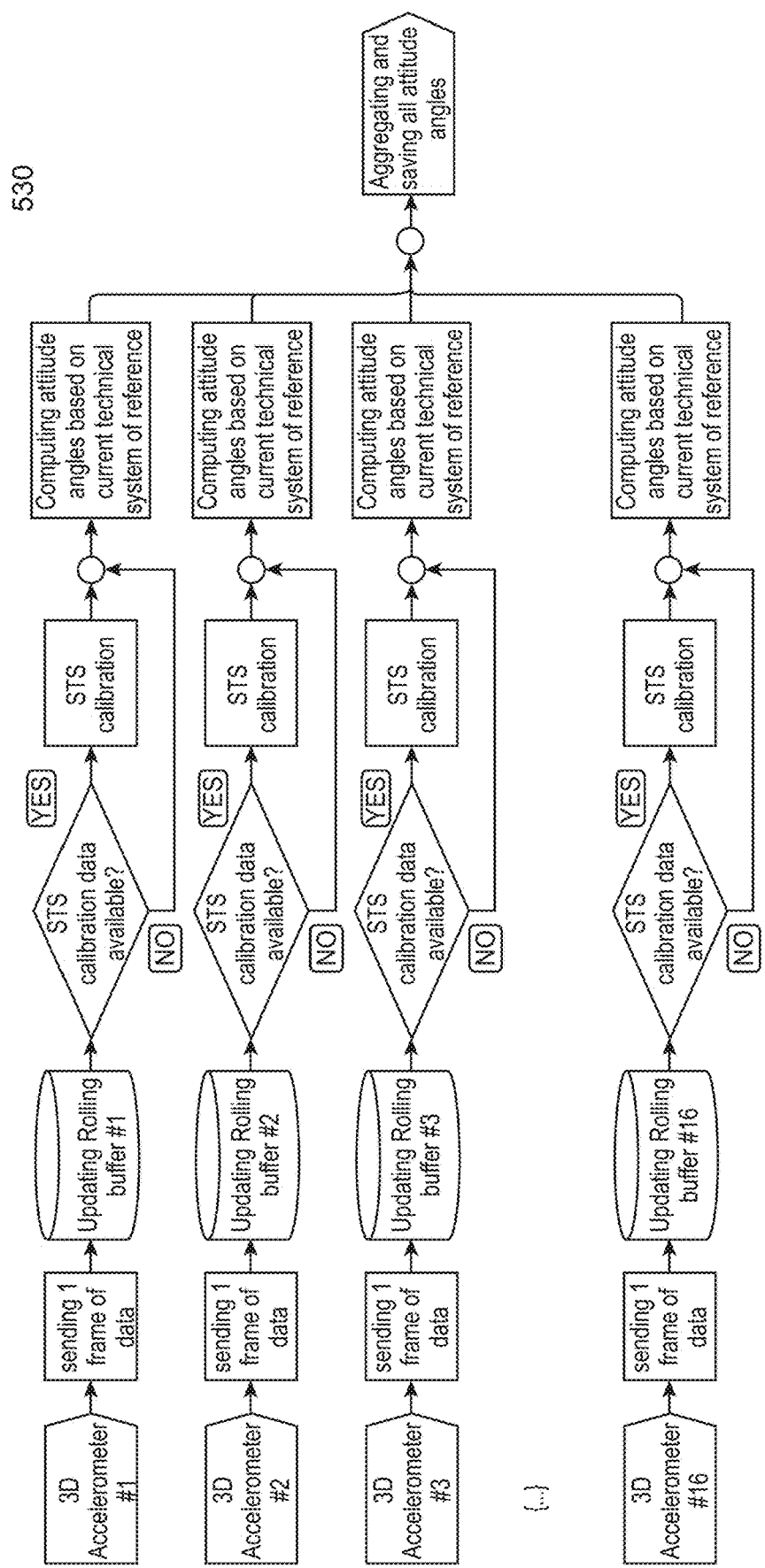
FIG. 5C shows a flowchart or process of performing attitude angle estimation.

Attitude angles (phi, teta) for each body segment are stored and used next in the above sub-components (4) (5) for the pose classification and scoring. If present, 3D joint angles are stored as well. FIG. 5C shows a flowchart or process of performing Attitude Angle Estimation.

All parameters computed in step (3) are compared with the models for all the poses described in step (1). In order to compute the degree of matching between one user's body segment and the reference value contained in one reference pose model (1), separate methods are applied:

M1:
 a) divide user's body segment averaged 3d acceleration by its Euclidean norm |a|=norm(a);
 b) compute the angle between the 3d vector |a| and the 3d vector contained in the reference pose (|arefl)
  delta_angle=a cos (|a| DOT |arefl)
  where DOT is the dot product.

M2 2:
 a) compute the difference between the body segments' attitude angles (teta, phi) calculated in (3) and the corresponding values saved in the reference pose model (1). M3: similarly to M1 1, if available, compute the overall degree of the agreement between the user's joint angles and the values saved in the reference pose model.

Figure 5D:
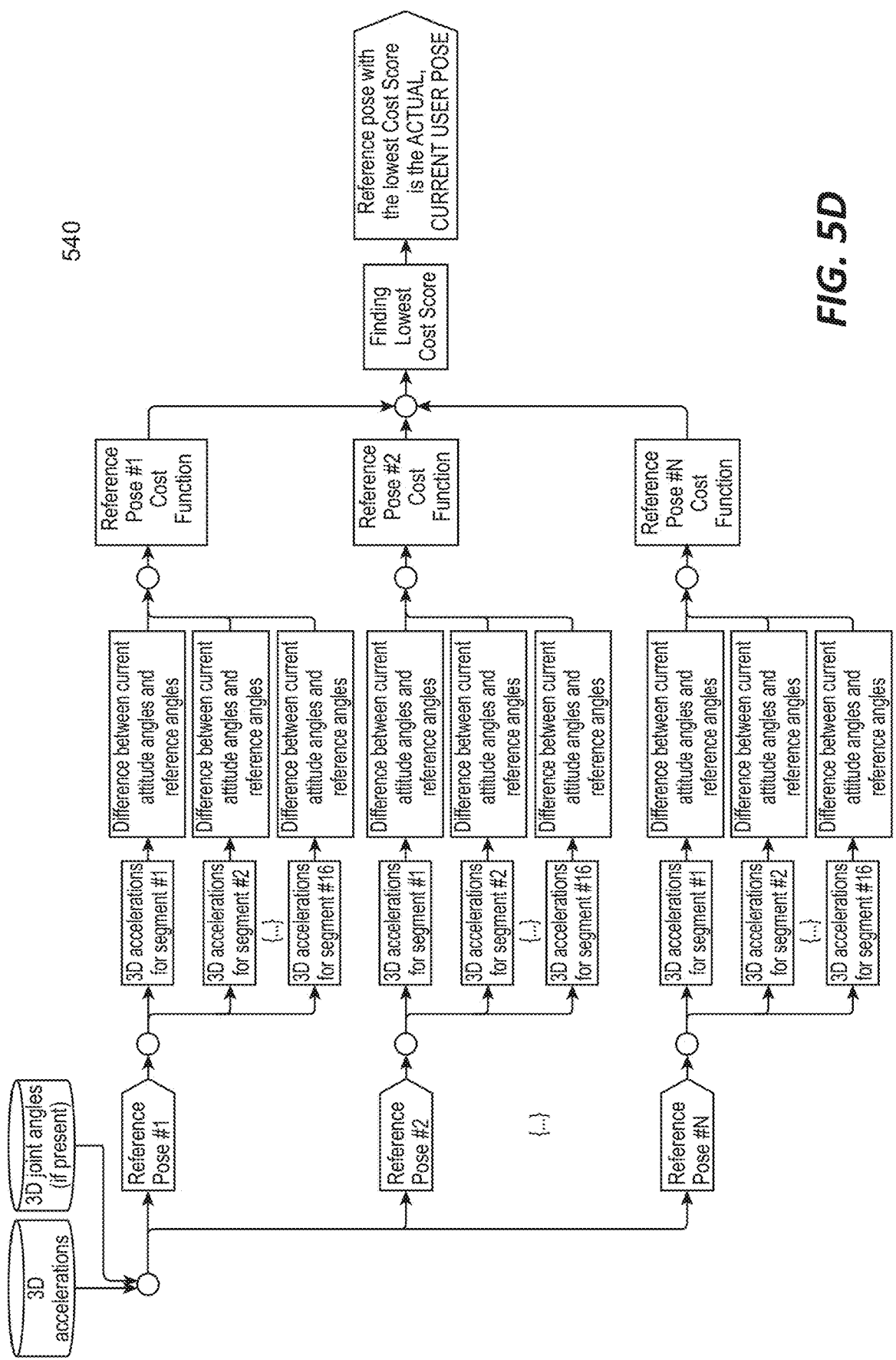
FIG. 5D shows a flowchart or process of an exemplary reference pose classifier.

Once (M1), (M2), and eventually (M3), are computed for each body segment, their values are combined into a per-pose cost function which will assign an overall agreement score among the user's current pose and the pose model used for the comparison. Once all pose models (1) agreement scores have been computed, the model pose with the highest agreement score is selected as the user's current pose. FIG. 5D shows a flowchart or process 540 of Reference Pose Classifier.

Once the current user's pose is classified (4) and matched with a pose model in the reference pool (1), it is possible to compute the following outcomes:
 O1: current user's pose MATCHES or NOT MATCHES the reference pose model;
 O2: overall pose matching score; and
 O3: per-body segment matching score.

Comparison metrics computed in (4) are combined in a segment- and pose-specific cost function representing the degree of matching between the user's current, actual pose and the reference.

In the following diagram is described the classification of every user body segment into:
 1) matching/not matching the reference pose model (Cost_score—O1, O2)
  cost_score=1 indicates that the body segment matches the reference model
  cost_score=0 indicates that the body segment does not match the reference model
 2) Overall percentage of agreement with the reference pose model (PA %—O2)

Figure 5E:
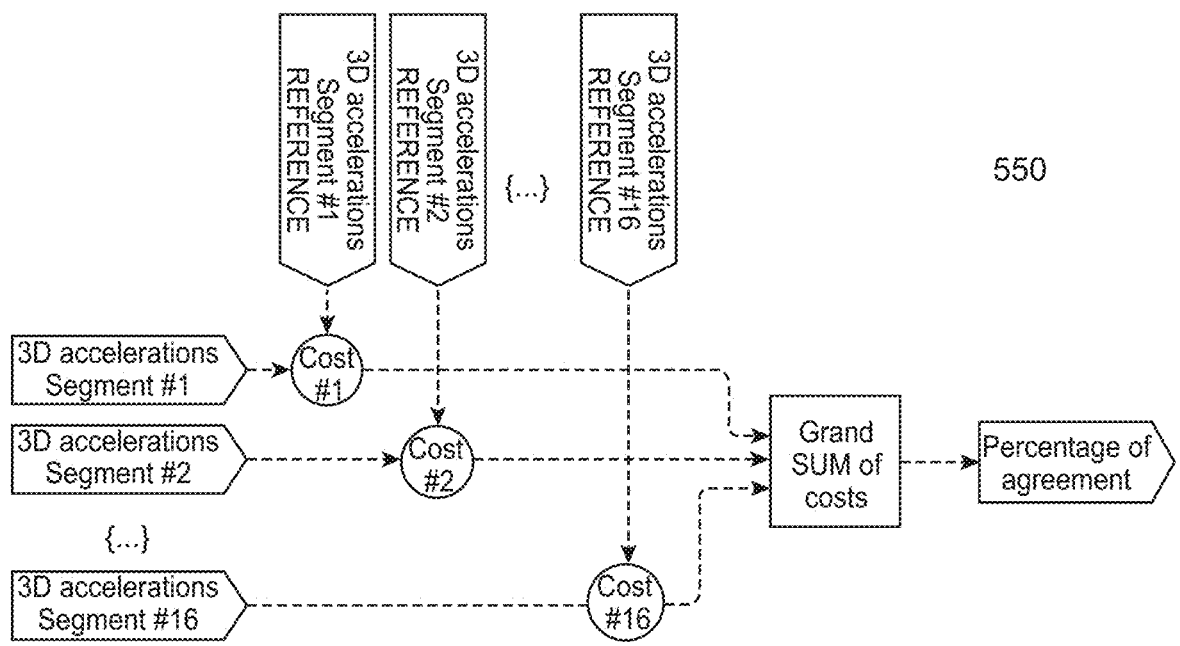
FIG. 5E shows a flowchart or process of estimating user pose scoring.
Figure 5E:
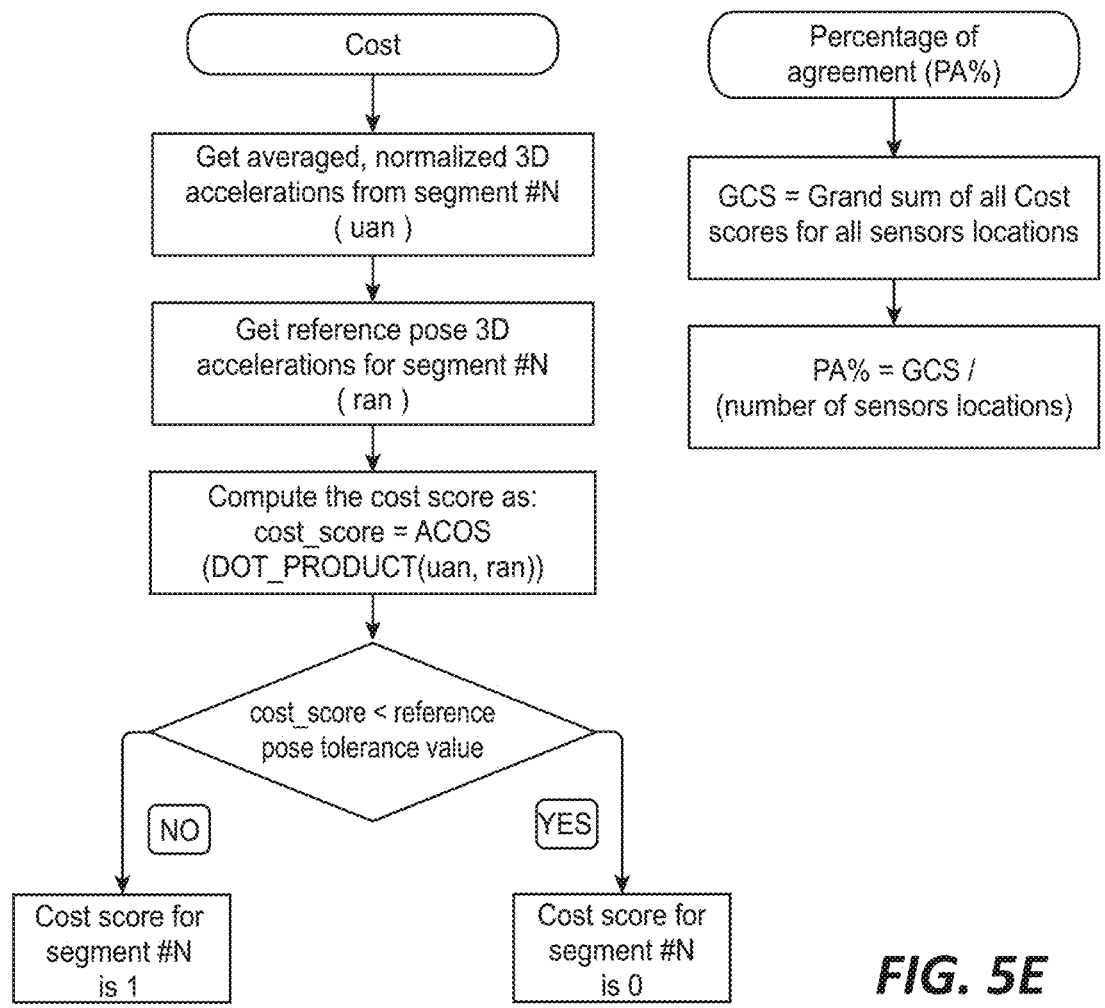
Figure 5F:
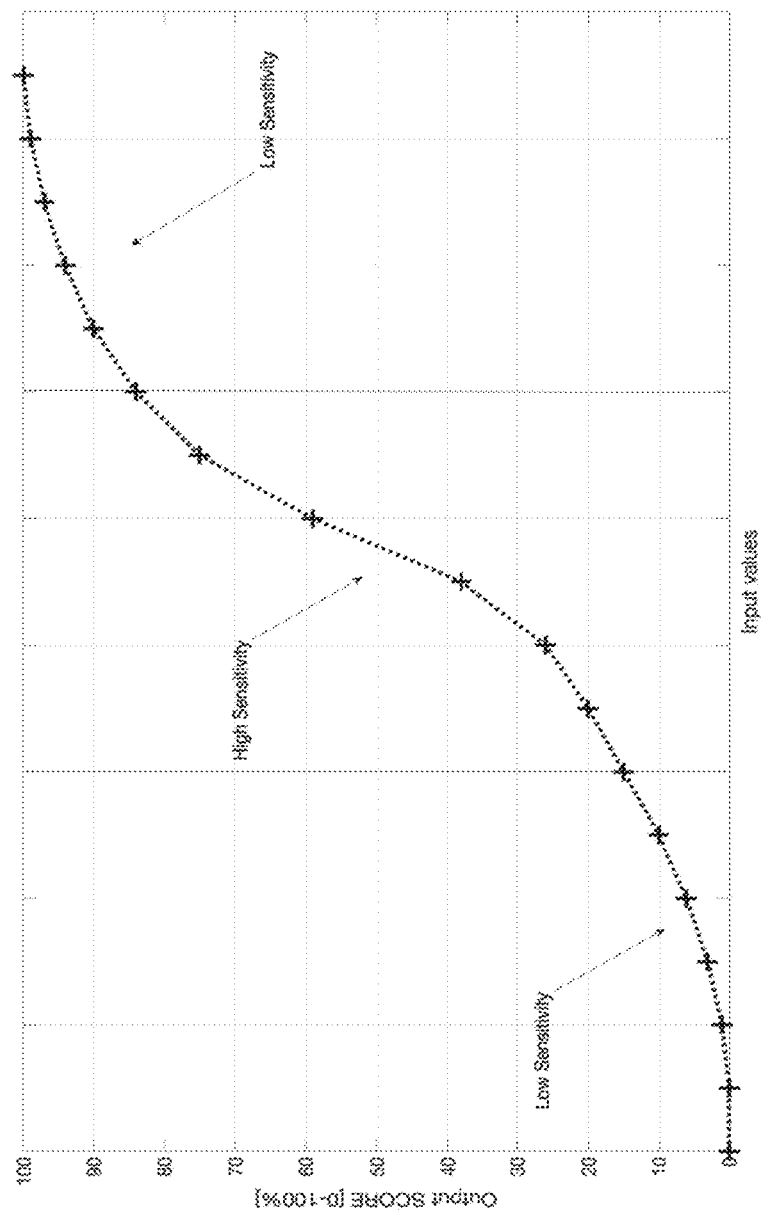
FIG. 5F shows an exemplary sigmoid transfer function.

Once the current user's pose is classified in step (4) and matched with a pose model in the reference pool (1), it is possible to compute the following outcomes as shown in a flowchart or process 550 FIG. 5E. Depending on the method applied, the per-segment and per-pose cost function can be unbounded and ranging from minus-infinity and plus-infinity. In order to normalize the score and make it at the same time comparable inter-user and inter-session and easily interpretable, a segment-specific and pose-specific sigmoid transfer function is applied to the cost function in order to translate the original unbounded values into bounded and easy-readable ones (e.g. 0%-100%). The sigmoid transfer function can be calibrated on the user specific level of ability in performing the pre-defined pool of poses (i.e. novice, amateur, expert, professional), so that the final score can be adapted to his experience progression.

As described above, one of the strategies to deal with the angular drifting error in PIVOT Mag Free is the pose reset. The idea is to exploit those moments while the user is doing a yoga pose (and it is still) to restart the sensor fusion algorithms. Note that the user stillness alone is not a sufficient condition to apply a sensor fusion reset in the mag free scenario. In fact, after the reset, each sensor fusion algorithm will take a different global reference frame. Therefore, the same global reference frame alignment procedure explained above needs to be performed. For doing so, it is necessary that the physical orientation of the sensor is known at the time the sensor fusion algorithm is reset. There are two reset strategies possible and hereafter they are called as soft pose reset and hard pose reset.

Figure 6A:
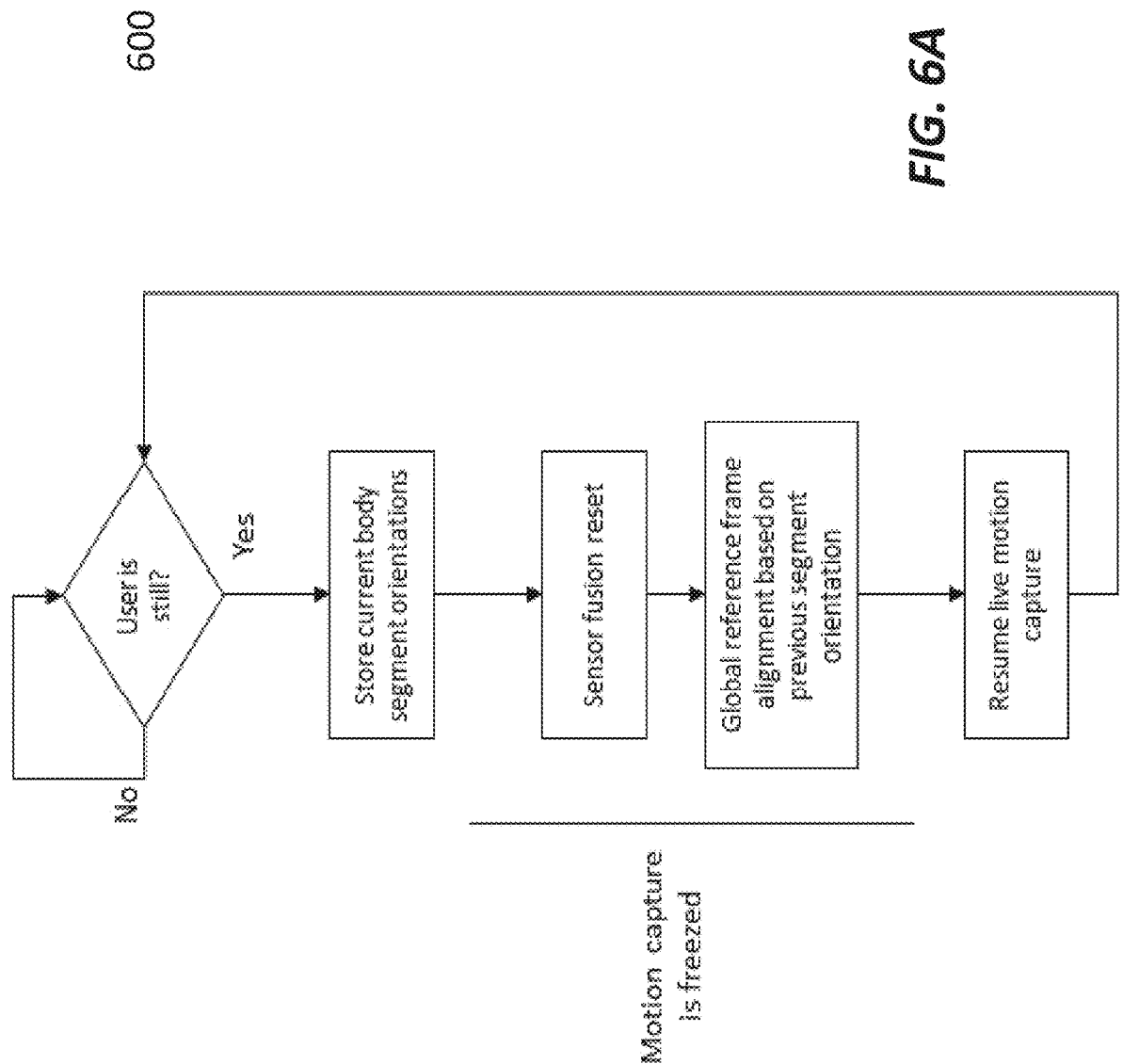
FIG. 6A shows a workflow or process of soft pose reset.

FIG. 6A shows a workflow or process 600 of soft pose reset. The process 600 may be launched every time a user is detected to be still. In that time instant, the current orientation of all the body segments of the user is stored and a sensor fusion algorithm reset is issued. The quaternions produced after the sensor fusion reset will be matched with the stored orientations before the reset in order to compute the previous global reference frame alignment procedure as described above. After the compensation, the motion capture session can be resumed.

The process 600 takes advantage in accuracy through the sensor fusion reset. However, it must be noted that the resuming condition for the sensor fusion algorithms could already be affected by some drift. Repeating this procedure many times may still result in a slow accumulation of drifting errors. In fact, the expectation of the soft pose reset is to make the drift slower but not to produce drift-less motion capture. Despite this drawback, however, this procedure is relatively simple to be implemented.

Figure 6B:
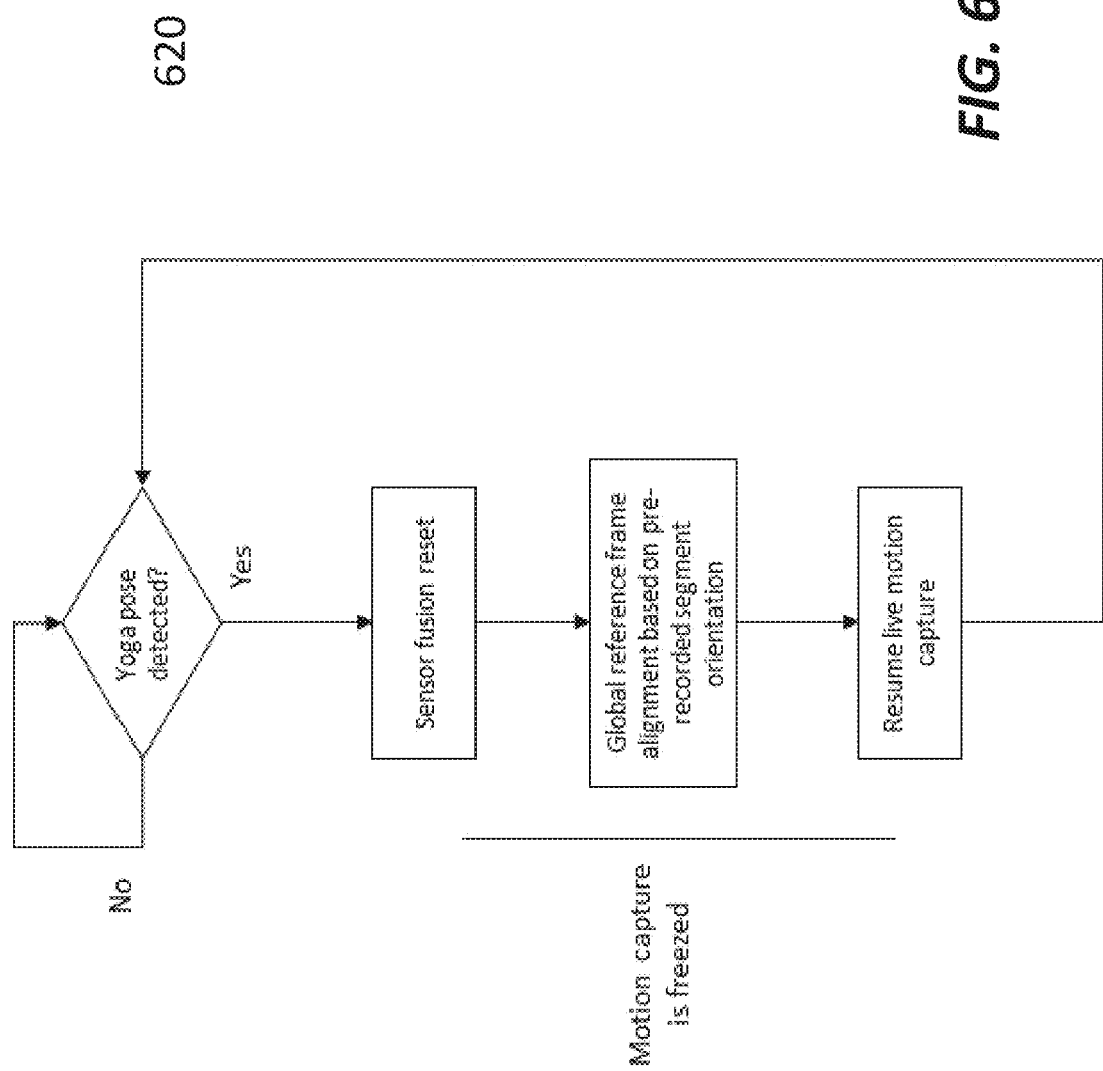
FIG. 6B shows a workflow or process of hard pose reset.

Another reset solution is implemented in PIVOT Mag Free in order to provide a drift-less estimate over a longer time window, which is called hard pose reset. This procedure is very similar to the soft pose reference, as shown in FIG. 6B with the following two main differences:

1. The reset must be triggered when the user is in a specific yoga pose (N-pose or yoga pose), the yoga pose detector described above is therefore used to trigger the hard pose reset.
2. The global reference frame alignment is computed based on reference (pre-recorded) body segment orientations. These reference poses can also be acquired with other (more accurate) motion capture systems, like stereo-photogrammetric systems.

The advantage of the hard pose reset over the soft pose reset is that not only sensor fusion algorithms are reset, but the reference pose used to resume the mocap is pre-recorded. This means that the reference pose is drift free, maybe even acquired with high accuracy systems. For this reason, triggering this procedure multiple times during will result in drift-less motion capture. However, this procedure is more complex and requires a specific yoga pose detection algorithm on top of it.

The description of the present invention is now focusing on what is referred herein as Double Tap Gesture Detection. The purpose of double tap gesture detection is to detect in real time a user performing specific gestures while wearing smart-clothing. Detected gestures are used to trigger specific actions on the App as instance play, and to pause the video. For double tap, the technique is intended to detect the act of tapping twice with one of the user hands' palm or fingers over one body segment. It is also possible to detect double tapping gestures over objects such as desks or walls. At least one involved body segment (the "active" or "tapping" hand and the "passive" or "tapped") is supposed to be instrumented with a smart-clothing.

The technique is based on the analysis of accelerometers and/or gyroscopes data coming from MEMS (micro electro mechanical systems) or NEMS (nano electro mechanical systems) contained within the smart clothing. In order to allow the detection of the broadest possible spectrum of combinations of tapping locations, data from all available sensors locations will be acquired and processed. This will allow to detect any combination of double-tapping events, both being performed with an instrumented body segment over another (T2), or with one instrumented body segment over a non-instrumented one (T1).

Examples of a tapping event happening between two instrumented body segments:

T2.1: instrumented left hand double-tapping on instrumented right hand
T2.2: instrumented left hand double-tapping on instrumented chest
T2.3: instrumented right hand double-tapping on instrumented left forearm Examples of a tapping event happening between one instrumented body segment and a non-instrumented body segment/object:

T1.1: instrumented left hand double-tapping on non-instrumented right hand
T1.2: non-instrumented left hand double-tapping on instrumented chest
T1.3: instrumented left hand double tapping on the desk
T1.4: instrumented right hand double tapping on the wall It is possible to detect only double taps in which the time intercurring the two tapping events is lower than a predefined threshold; such threshold can be altered while the algorithm is already running.

The technique is composed by a chain of 4 specific functional blocks:

FB1: sensor data collection and buffering;
FB2: sensor data processing;
FB3: Double-Tap event detection on a single sensor; and
FB4: Double-Tap events aggregator and classifier.

Figure 7A:
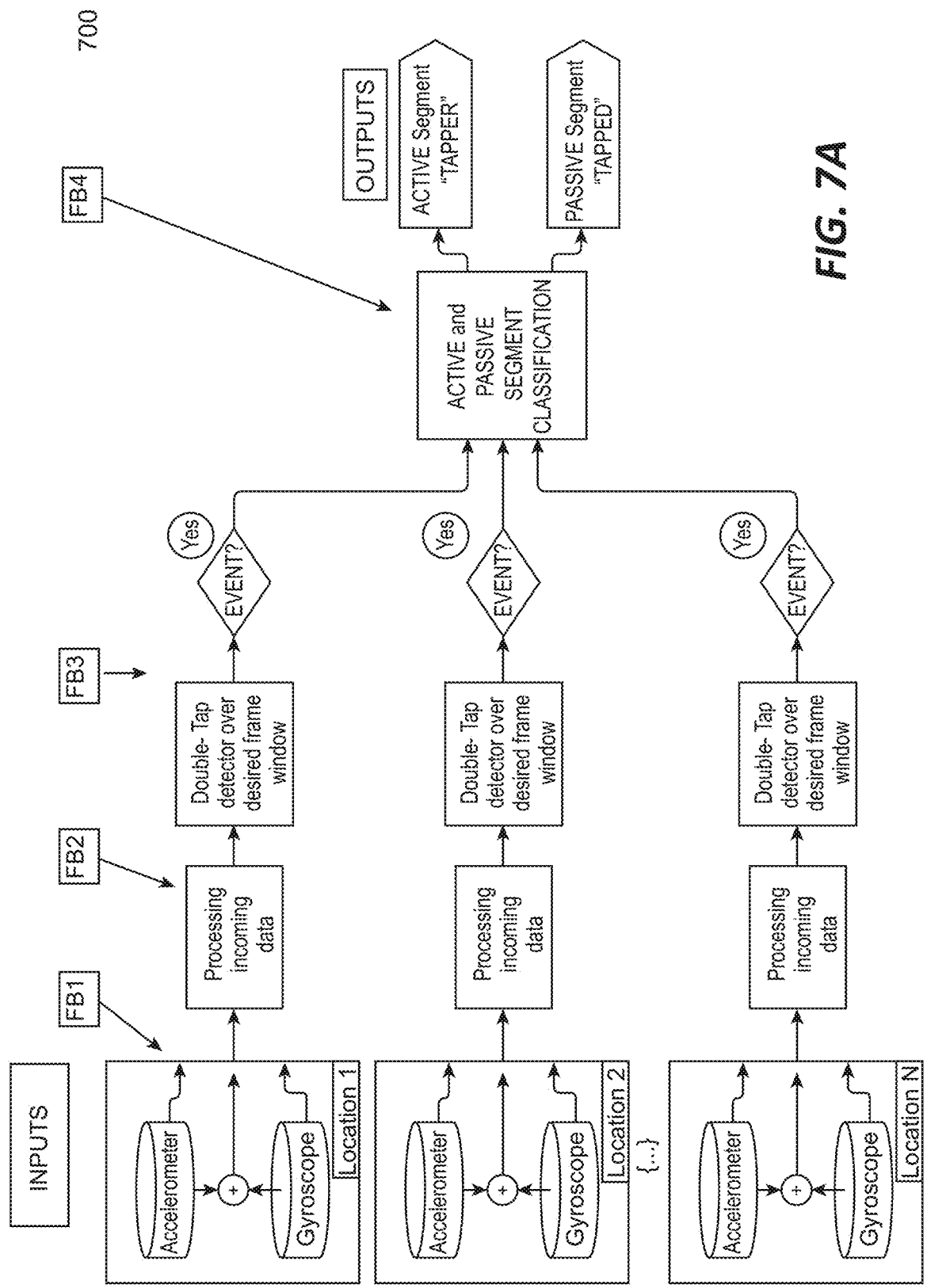
FIG. 7A shows a flowchart or process of double tap gesture detection.

FIG. 7A shows a flowchart or process 700 of double tap gesture detection. Data from all sensors locations (e.g. left hand, right hand, chest) is collected and streamed to the detection algorithm using one rolling data buffer (FIFO) per sensor, per location. The buffer will contain as much data as the maximum allowed duration of the double tap. As instance, considering:

100 Hz sampled data; and
a maximum allowed time of 1 second for the second tap to happen.

The technique is composed by a chain of 4 specific functional blocks. The rolling buffer contains 100 (100 Hz*1 sec) samples per satellite location. For every sensor location, the algorithm will be aware of the number and type of sensors present:

S1: Accelerometer
S2: Gyroscope
S3: Accelerometer AND Gyroscope

Depending on the scenario (S1-S3), the algorithm will apply different, specific signal processing methods (e.g. high-pass or low-pass filtering) in order to remove spurious noise and to isolate only the signals' spectra band required. Additional postprocessing methods can be applied in order to maximize the chances of double tap detection; in the following examples:

Gyroscopes data will be processed to compute the frame-by-frame norm; norm is the frame-by-frame Euclidean norm of the gyroscope data.

(f1)

$$|g| = \sqrt{g_x^2 + g_y^2 + g_z^2}$$

Accelerometers data will be processed to compute the normalized jerk; normalized jerk is the Euclidean norm of the time-derivative of the acceleration data.

(f2a)

$$\underline{j} = \frac{da\_(t)}{d(t)}$$

(f2b)

$$|j| = \sqrt{j_x^2 + j_y^2 + j_z^2}$$

After processing the incoming signal, an iterative, dynamic threshold approach will be applied on the buffered and processed data. After setting the amplitude threshold value, a local maxima detection algorithm will seek the buffered data for signal peaks above the set threshold. A local maximum is identified by the following rules:

R1: three subsequent frames above the set threshold
R2: data at frame t has a lower amplitude than data at frame t+1

R3: data at frame t+1 has a higher amplitude than data at frame t+2 Considering the number of above-threshold local maxima found, the signal can be classified as:
E1: no local maxima are found higher than the threshold;
E2: 1 local maximum is found higher than the threshold;
E3: 2 local maxima are found higher than the threshold; and
E4: more than 2 local maxima are found higher than the threshold.

If 2 or more local maxima are found (E3, E4), the iterative process will stop.

If 2 local maxima are found (E3), a double tap event occurring in the current location is identified.

If 1 or none local maxima are found (E1, E2), the amplitude threshold value is lowered by a predefined value (e.g. 5%) and the local maxima algorithm is iterated again.

Figure 7B:
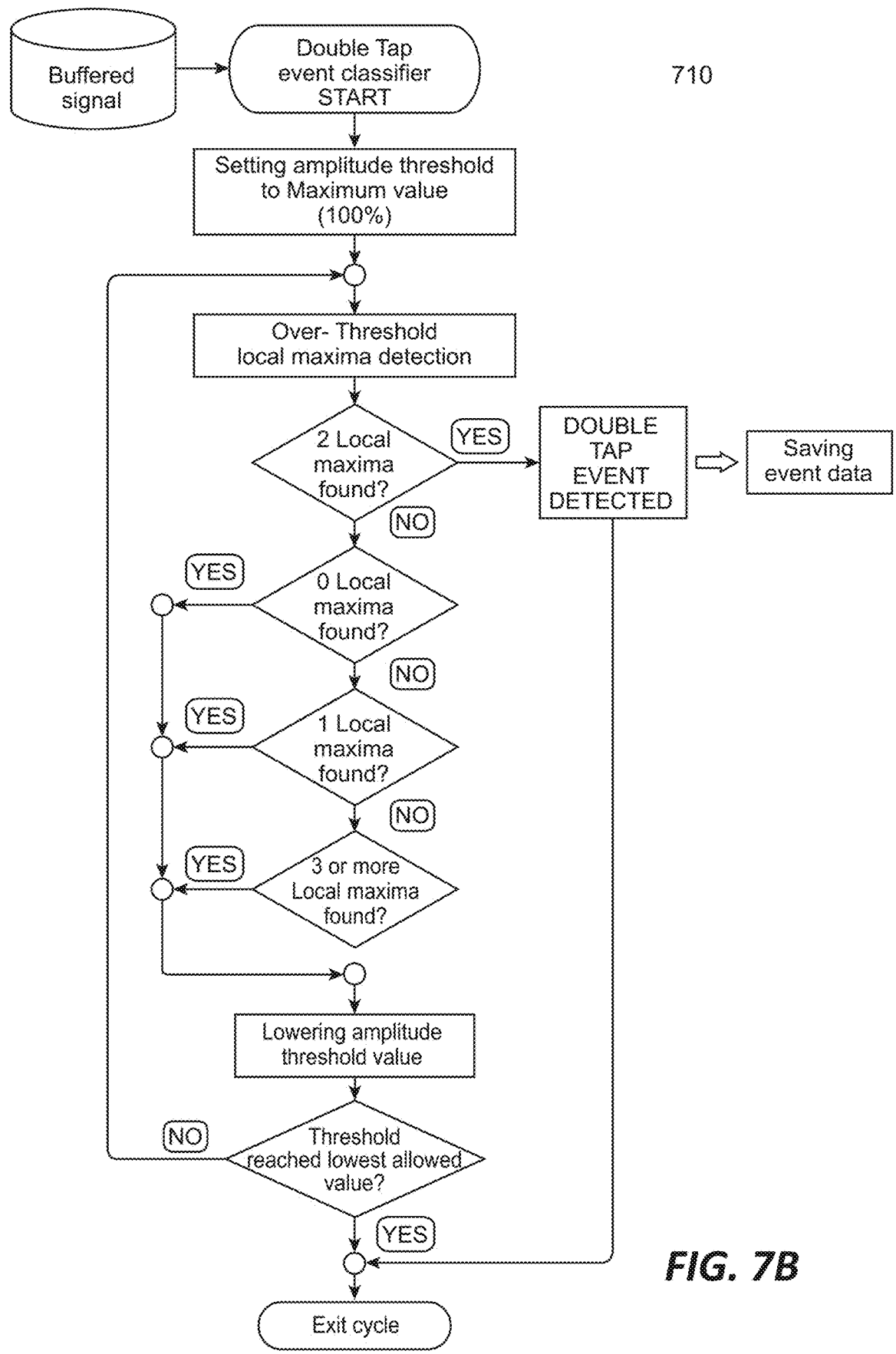
FIG. 7B shows a flowchart or process of double tap event detection.
Figure 7C:
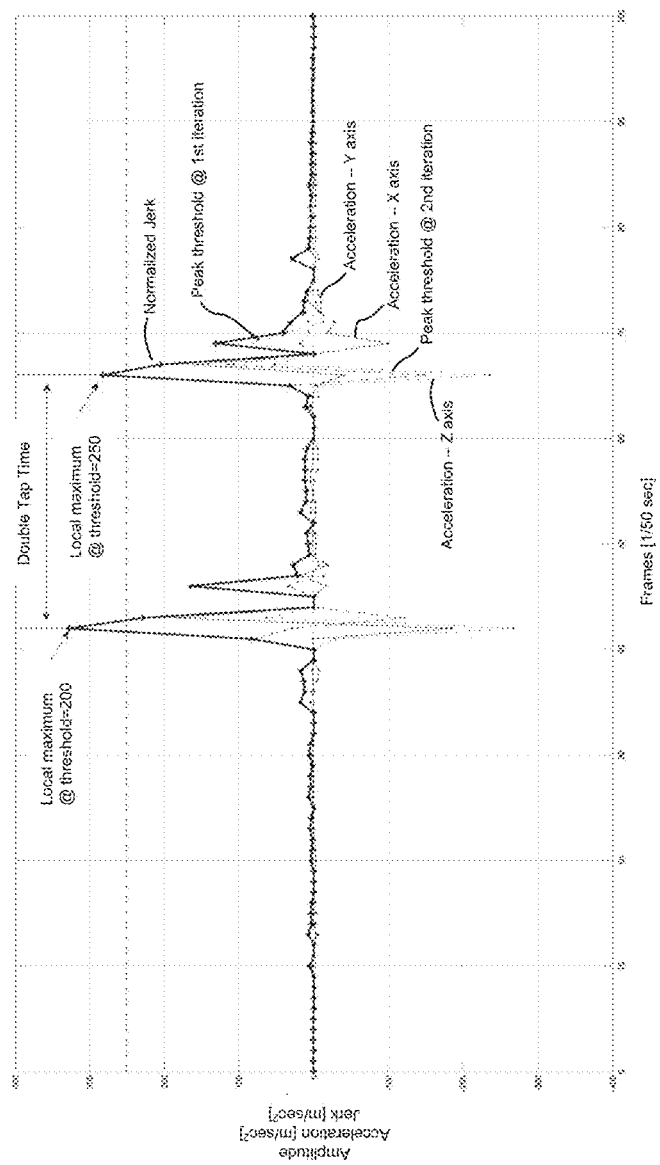
FIG. 7C shows an example of double tap event found on accelerometer data after applying two different peak thresholds.
Figure 7D:
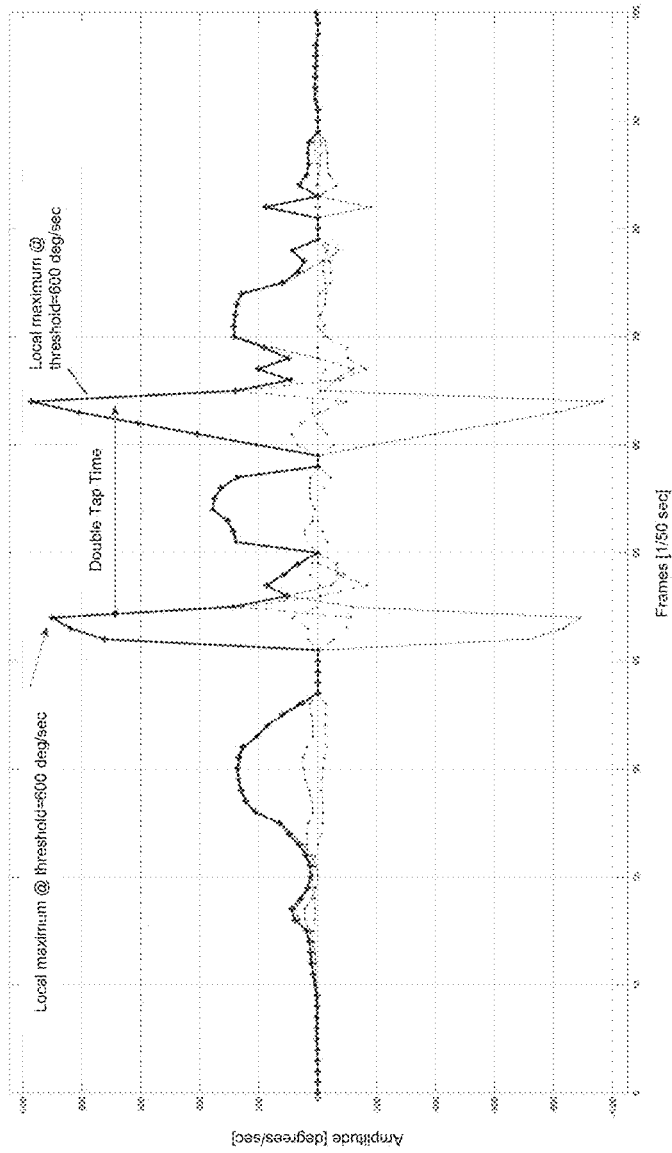
FIG. 7D shows an example of double tap event found on gyroscope data.

This method is iterated until one of the following events occur:
E3: 2 local maxima are found;
E5: the amplitude threshold reached the lowest value allowed (e.g. 200 deg/sec). FIG. 7B shows a flowchart or process 710 Double Tap Event Detection Flowchart. FIG. 7C shows an example of double tap event found on accelerometer data after applying two different peak thresholds. FIG. 7D shows an example of double tap event found on gyroscope data.

Based on the events occurred (E1-E4), a first classification of the signal takes place on the sensor data:
E1: NO DOUBLE TAPPING occurred, as no related signal's pattern landmarks are found
E2: NO DOUBLE TAPPING occurred, as no related signal's pattern landmarks are found
E3: DOUBLE TAPPING EVENT OCCURRED
E4: NO DOUBLE TAPPING occurred, as the signal's pattern found is related to motion noise or non-conforming gestures (e.g. triple taps, hands shaking).

If a double tap event is found on 2 or more sensors locations, the data from the sensors which generated the events is passed to the active/passive segment classifier.

The active/passive segment classifier will analyze the data and provide:
O1: if present, which sensor location was the "active" tapping segment (or "tapper")
O2: if present, which sensor location was the "passive" tapping segment (or "tapped").

Figure 7E:
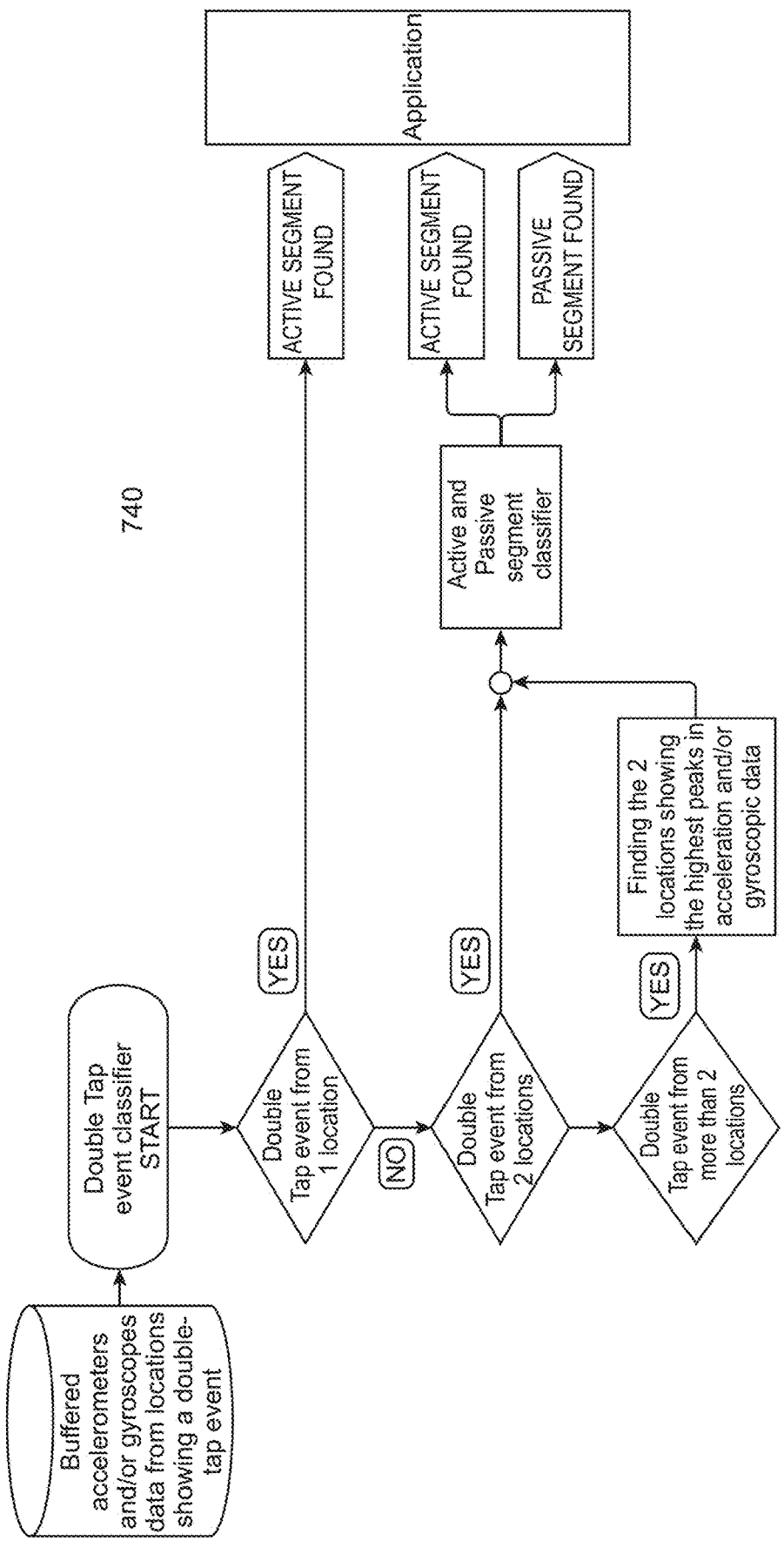
FIG. 7E shows a flowchart or process of double tap event details classifier.

If more than two sensors locations generated the double tap event (E3), as instance due to a particular fast user motion, the classifier will be capable of detecting the actual O1 and O2 by analyzing and comparing signal patterns characteristics from all sensors locations which generated the double tap event (E3). FIG. 7E shows a flowchart or process 750 of double tap event details classifier. Once the double-tapping event is detected and classified in all of its parameters (time, O1, O2), the algorithm communicates the decoded event to the App, which applies the specified action. As instance:

Example 1

Tapping Time: 0.4 seconds;
O1: left hand is the active tapper;
O2: right hand is the passive tapper; and
This combination of events is associated to the app's command: "Stop video".

Example 2

Tapping time: 0.5 seconds;
O1: right hand is the active tapper;
O2: no events; and
This combination of events is associated to the app's command "Resume Video".

The App or the algorithms described above are preferably implemented in software, but can also be implemented in hardware or a combination of hardware and software. The implementation of the App or the algorithms can also be embodied as computer readable code on a computer readable medium. The computer readable medium is any data storage device that can store data which can thereafter be read by a processor or a computer system. Examples of the computer readable medium include read-only memory, random-access memory, CD-ROMs, DVDs, magnetic tape, optical data storage devices, and carrier waves. The computer readable medium can also be distributed over network-coupled computer systems so that the computer readable code is stored and executed in a distributed fashion.

The present invention has been described in sufficient details with a certain degree of particularity. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the foregoing description of embodiments.

We claim:

1. An article of clothing comprising:
a layer of material;
a plurality of sensor modules respectively attached to designated locations on the layer of material, wherein each of the sensor modules corresponds to a designated body part of a user, at least one of the sensor modules is designated as a hub module and the rest of the sensor modules are designated as satellite modules, each of the satellite modules includes a microcontroller, at least an inertial sensor and a transceiver for intercommunication with the hub module, the hub module includes a microcontroller, at least an inertial sensor and a transceiver for intercommunication with the satellite modules and another transceiver for communicating with an external computing device; and
a plurality of conductive threads embedded in the layer of material, wherein one or more of the conductive threads provide a communication medium between or among the sensor modules.

2. The article of clothing as recited claim 1, wherein each of the sensor modules is responsible to capture a motion of the designated body part when the user wears the clothing.

3. The article of clothing as recited claim 2, wherein the conductive threads are not visible from outside of the clothing.

4. The article of clothing as recited claim 3, wherein each of the conductive threads is composed of low-resistivity copper core with nano fiber insulation.

5. The article of clothing as recited claim 3, wherein each of the conductive threads has textile properties, composed of low-resistivity with less than 1.5 Ohms per meter.

6. The article of clothing as recited claim 5, wherein a diameter of each of the conductive thread is around 0.32 millimeters.

7. The article of clothing as recited claim 3, wherein each of the conductive threads goes a zigzag pattern to allow more flexibilities when the user moves around.

8. The article of clothing as recited claim 1, wherein the clothing appears and feels like regular athletic-leisure clothes with electronics hidden and unfelt.

9. The article of clothing as recited claim 8, wherein the layer of material has an inner side, the sensor modules are respectively attached to the designated locations on the inner side of the layer of material.

10. The article of clothing as recited claim 1, wherein the clothing is made in a shirt.

11. The article of clothing as recited claim 1, wherein the clothing is made in a pair of pants.

12. The article of clothing as recited claim 1, wherein the clothing is made in a pair of gloves.

13. The article of clothing as recited claim 1, wherein the clothing is made in a pair of socks.

\* \* \* \* \*